United States Patent
Guillonneau et al.

(10) Patent No.: US 12,054,743 B2
(45) Date of Patent: Aug. 6, 2024

(54) METHOD FOR OBTAINING T CELLS FROM PLURIPOTENT STEM CELLS, AND USES THEREOF

(71) Applicants: CENTRE NATIONAL DE LA RECHERCHE SCIENTIFIQUE, Paris (FR); INSERM (Institut National de la Santé et de la Recherche Médicale), Paris (FR); CENTRE HOSPITALIER UNIVERSITAIRE DE NANTES, Nantes (FR); UNIVERSITÉ DE NANTES, Nantes (FR)

(72) Inventors: Carole Guillonneau, La Chevrolière (FR); Laurent David, Nantes (FR); Léa Flippe, Piriac sur Mer (FR)

(73) Assignees: CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR); CENTRE HOSPITALIER UNIVERSITAIRE DE NANTES, Nantes (FR); UNIVERSITÉ DE NANTES, Nantes (FR)

( * ) Notice: Subject to any disclaimer, the term of this patent is extended or adjusted under 35 U.S.C. 154(b) by 954 days.

(21) Appl. No.: 16/982,881

(22) PCT Filed: Mar. 22, 2019

(86) PCT No.: PCT/FR2019/050667
§ 371 (c)(1),
(2) Date: Sep. 21, 2020

(87) PCT Pub. No.: WO2019/180394
PCT Pub. Date: Sep. 26, 2019

(65) Prior Publication Data
US 2021/0002612 A1    Jan. 7, 2021

(30) Foreign Application Priority Data
Mar. 23, 2018 (FR) .................................. 1852531

(51) Int. Cl.
*C12N 5/0783*    (2010.01)
*A61K 35/17*    (2015.01)

(52) U.S. Cl.
CPC ............ *C12N 5/0637* (2013.01); *A61K 35/17* (2013.01); *C12N 5/0636* (2013.01);
(Continued)

(58) Field of Classification Search
CPC .......................... C12N 5/0637; C12N 5/0636; C12N 2500/90; C12N 2501/115;
(Continued)

(56) References Cited

FOREIGN PATENT DOCUMENTS

| | | | |
|---|---|---|---|
| WO | 2006021950 A1 | 3/2006 |
| WO | 2010051634 A1 | 5/2010 |

(Continued)

OTHER PUBLICATIONS

Maxim A. Vodyanik, James A. Thomson, Igor I. Slukvin; CD43 Defines Early Hematopoietic Progenitors Derived from Human Embryonic Stem Cells (hESC). Blood 2004; 104 (11): 3216) (Year: 2004).*

(Continued)

*Primary Examiner* — Jeremy C Flinders
*Assistant Examiner* — Thomas R. Amick
(74) *Attorney, Agent, or Firm* — Maier & Maier, PLLC

(57) ABSTRACT

A method for obtaining a population of T cells from pluripotent stem cells, which includes a first step of obtaining hematopoietic stem cells and a second step of obtaining T cells. Also, the cell populations thus obtained according to this method and these cell populations for use as a medicament.

14 Claims, 9 Drawing Sheets

(52) U.S. Cl.
CPC .... *C12N 2500/90* (2013.01); *C12N 2501/115* (2013.01); *C12N 2501/125* (2013.01); *C12N 2501/155* (2013.01); *C12N 2501/165* (2013.01); *C12N 2501/2303* (2013.01); *C12N 2501/26* (2013.01); *C12N 2501/42* (2013.01); *C12N 2501/60* (2013.01); *C12N 2506/11* (2013.01); *C12N 2506/45* (2013.01); *C12N 2510/00* (2013.01)

(58) Field of Classification Search
CPC ........ C12N 2501/125; C12N 2501/155; C12N 2501/165; C12N 2501/2303; C12N 2501/26; C12N 2501/42; C12N 2501/60; C12N 2506/11; C12N 2506/45; C12N 2510/00; C12N 2500/38; C12N 2500/99; C12N 2501/734; A61K 35/17
See application file for complete search history.

(56) References Cited

FOREIGN PATENT DOCUMENTS

| WO | 2014165707 A2 | 10/2014 |
|---|---|---|
| WO | 2014180943 A1 | 11/2014 |
| WO | 2017100403 A1 | 6/2017 |

OTHER PUBLICATIONS

Pettinato, Giuseppe, et al. Engineering Strategies for the Formation of Embryoid Bodies from Human Pluripotent Stem Cells. Stem Cells and Development. Jul. 15, 2015; 24(14):1595-609.
Petersen, Christopher T., et al. Improving T-cell expansion and function for adoptive T-cell therapy using ex vivo treatment with PI3Kδ inhibitors and VIP antagonists. Blood Advances. Feb. 13, 2018; 2(3):210-223.
Boursier, Guilaine, et al. Utilisation des lymphocytes T regulateurs en therapies cellulaires dans les maladies auto-immunes [Use of regulatory T lymphocytes in cell therapy in autoimmune diseases]. Med Sci (Paris). Aug.-Sep. 2012; 28(8-9):757-63. French. English translation provided.
Baine, Ian, et al. Helios induces epigenetic silencing of IL2 gene expression in regulatory T cells. J Immunol. Feb. 1, 2013; 190(3):1008-16.
Bonini, Chiara, et al. Adoptive T-cell therapy for cancer: The era of engineered T cells. European Journal of Immunology. Sep. 2015; 45(9):2457-69.
Cavazzana-Calvo, Marina, et al. Hematopoiese humaine : des cellules CD34 aux lymphocytes T [Human hematopoiesis: from CD34 cells to T lymphocytes]. Med Sci (Paris). Feb. 2007; 23(2):151-9. French. English translation provided.
Chang, Chia-Wei, et al. Broad T-Cell Receptor Repertoire in T-Lymphocytes Derived from Human Induced Pluripotent Stem Cells. PLoS One. May 14, 2014; 9(5):e97335.
Chung, Young, et al. Human Embryonic Stem Cell Lines Generated without Embryo Destruction. Cell Stem Cell. Feb. 7, 2008; 2(2):113-7.
Gill, Saar, et al. Going viral: chimeric antigen receptor T-cell therapy for hematological malignancies. Immunological Reviews. Jan. 2015; 263(1):68-89.
Haque, Rizwanul, et al. Programming of regulatory T cells from pluripotent stem cells and prevention of autoimmunity. J Immunol. Aug. 1, 2012; 189(3):1228-36.
Haque, Mohammad, et al. Development of Stem Cell-derived Antigen-specific Regulatory T Cells Against Autoimmunity. Journal of Visualized Experiments. Nov. 8, 2016; (117):54720.
Holmes, Roxanne, et al. The OP9-DL1 System: Generation of T-Lymphocytes from Embryonic or Hematopoietic Stem Cells in Vitro. Cold Spring Harbor Laboratory Press. Feb. 2009; 2009(2):pdb.prot5156.
Jensen, Michael C. and Riddell, Stanley R. Designing Chimeric Antigen Receptors to Effectively and Safely Target Tumors. Curr Opin Immunol. Apr. 2015; 33:9-15.
Kato, Shingo, et al. Possible Therapeutic Application of Targeting Type II Natural Killer T Cell-Mediated Suppression of Tumor Immunity. Frontiers in Immunology. Feb. 22, 2018; 9:314.
Lei, Fengyang, et al. T lineage differentiation from induced pluripotent stem cells. Cellular Immunology. 2009; 260 (1):1-5.
MacDonald, Katherine G., et al. Alloantigen-specific regulatory T cells generated with a chimeric antigen receptor. The Journal of Clinical Investigation. Apr. 1, 2016; 126(4):1413-24.
Passerini, Laura, et al. (2017) "Forkhead-Box-P3 Gene Transfer in Human CD4+ T Conventional Cells for the Generation of Stable and Efficient Regulatory T Cells, Suitable for Immune Modulatory Therapy." Frontiers in Immunology 8:1282.
Picarda, Elodie, et al. Transient antibody targeting of CD45RC induces transplant tolerance and potent antigen- specific regulatory T cells. JCI Insight. Feb. 9, 2017; 2(3):e90088.
Srivastava, Shivani, et al. Engineering CAR-T cells: Design concepts. Trends in Immunology. Aug. 2015; 36(8):494-502.
Haque, Mohammad, et al. Stem cell-derived tissue-associated regulatory T cells ameliorate the development of autoimmunity. Scientific Reports. Feb. 5, 2016; 6:20588.

\* cited by examiner

METHOD FOR OBTAINING T CELLS FROM PLURIPOTENT STEM CELLS, AND USES THEREOF

FIELD

The invention pertains to the technical field of immunology. More particularly, the invention relates to methods for obtaining T cells, in particular regulatory T cells (Treg) and/or effector T cells (Teff), from pluripotent stem cells.

BACKGROUND

T lymphocytes, or T cells, are cells that play a central role in the secondary immune response. They get their name from their differentiation that occurs in the thymus. When they enter this organ, they quickly lose their potential to differentiate into a B lymphocyte, due to the interaction of progenitors expressing Notch1, with Notch Delta-1 and Delta-4 ligands, which are strongly and exclusively expressed in the thymus (Cavazzana-Calvo 2007). Among T cells, different sub-populations have been identified, especially regulatory T cells "Tregs", effector T cells "Teff" and Natural Killer T lymphocytes "NKT".

T lymphocytes may for example be identified by the expression of CD3, CD4, CD8 and/or the T cell receptor "TCR".

Regulatory T cells, called Treg cells, are usually characterized by the expression of Foxp3 (Forkhead box P3), a transcription factor essential for their differentiation during hematopoiesis. Treg cells represent 5 to 10% of the CD4+ T cell subpopulation in mice, rats and humans, with approximately 1 to 2% of these Treg cells circulating in the peripheral circulation (Hague 2016). The great capacity of Treg cells to control the immune response has led to consider them as tools for controlling the unwanted immune response, especially in the context of transplants, grafts or to treat autoimmune and inflammatory diseases. Clinical trials have thus already been conducted and have shown encouraging results for cellular therapies with Tregs, for example in the treatment of GvHD (graft versus host disease), following transplantation of allogeneic hematopoietic stem cells, organ transplantation, in patients with type 1 diabetes, chronic inflammatory diseases, as well as in patients who have undergone a kidney or liver transplant (Passerini 2017).

Effector T lymphocytes are able to produce various cytokines and to adopt a cytotoxic activity allowing them to recognize and destroy cells considered as foreign to the organism. They play an important role in the rejection of transplants and in the death of tumor cells or cells infected with viruses.

NKT cells constitute about 0.2% of peripheral blood T lymphocytes. They have the particularity of exhibiting both characteristics specific to T cells, such as the expression of a TCR or the type-specific response to antigens, and characteristics associated with Natural Killer "NK" cells of the innate immunity, such as expression of NK1.1 or CD56 (Kato 2018).

The therapeutic use of T cells is booming. There is therefore a need for culture methods allowing to obtain efficient T cells and in sufficient quantity to allow their therapeutic application.

Several protocols allowing to generate T cells from pluripotent cells have been implemented and are in particular described by international applications WO 2017/100403, WO 2014/165707, WO 2010/051634, as well as by the scientific publications by Chang and al. (2014), Lei et al. (2009) and Holmes et al. (2009).

It is known that the culture of pluripotent stem cells in three dimensions, for example in a biomaterial such as a hydrogel matrix, allows to closely reproduce the interactions and physical constraints which are exerted during the normal development of the embryo. These "improved" conditions result in obtaining cell populations with phenotypes more representative of those observed during development and differentiation in a living organism.

Furthermore, the introduction of the FOXP3 gene associated with the one allowing expression of the TCR, through lentivirus, into murine induced pluripotent stem cells cocultured with cells expressing Notch ligands (cell lines OP9-DLL1 and OP9-DLL4) has enabled the production of CD4+CD3+CD25+Foxp3+ or CD8+CD3+CD25+Foxp3+ Treg, and carrying the TCR (TCR+) (Haque 2012; Haque 2017). These results obtained in mice implied the use of thymus fragments, which would not be possible for a therapeutic application in humans.

Thus, there is a need for a protocol allowing to generate, from pluripotent stem cells, T cells, especially Treg cells, directly usable in therapy in humans and which do not imply thymus fragments.

Furthermore, to the present knowledge of the inventors, there are no published methods allowing to obtain a significant expression of the TCR in the populations of Teff cells and of CD4−CD8−CD3+TCRab+ T cells.

Moreover, there is a need for a protocol allowing to obtain a T cell population comprising at the same time Treg, Teff and CD4−CD8−CD3+TCRab+ T cells.

Thus, there is a need for a simple method enabling to obtain T cells, especially Treg, Teff and CD4−CD8−CD3+TCRab+ T cells, in large number, especially for therapeutic applications. There is especially a need for a simple method enabling to obtain T cells in large number expressing a chimeric antigen receptor or "CAR", which can be used in cell therapy, for example for the treatment of graft rejection, graft versus host disease, autoimmune disease, inflammatory disease or cancer. In particular, there is a need for a simple method enabling to obtain Treg cells in large number expressing a chimeric antigen receptor or "CAR", for example an anti-HLA CAR, which can be used in cell therapy, for example for the treatment of graft rejection or graft versus host disease.

SUMMARY

The present invention relates to a method for obtaining a population of T cells from pluripotent stem cells, the population thus obtained, the population thus obtained for its use as a medicament, as well as the population thus obtained for its use in the treatment of a pathology related to an immune dysregulation such as infections, autoimmune diseases, inflammatory diseases, cancer, allergies, graft rejection, graft versus host disease.

A first object of the invention is a method for obtaining a population of T cells from pluripotent stem cells, comprising the following steps:

a) culturing pluripotent stem cells under conditions allowing to obtain embryoid bodies comprising at least 5% of CD34+CD43+ cells;

b) dissociating said embryoid bodies;

c) culturing said dissociated embryoid bodies with at least one Notch ligand, preferably in coculture with cells expressing at least one Notch ligand;

d) carrying out, during step c), the introduction of a vector comprising at least one nucleic acid sequence encoding Foxp3 in at least one cell, preferably when at least 15% of the cell population exhibits the CD43− phenotype.

According to an embodiment, the embryoid bodies obtained in step a) comprise at least 15% of CD34+CD43+ cells.

According to an embodiment, step a) is carried out for at least 9 days, preferably for 9 to 12 days.

According to an embodiment, step a) is carried out in a serum free culture medium, comprising BMP, FGF2, VEGF, SCF, Flt3-L and/or IL-3.

According to an embodiment, the dissociated embryoid bodies, obtained at the end of step b), are cultured in a culture medium comprising SCF, Flt3-L and/or IL-7, for at least 15 days.

According to an embodiment, step d) of introducing a vector comprising a nucleic acid sequence encoding Foxp3 is carried out between day Dd8 and day Dd12 of step c).

According to an embodiment, the vector of step d) is a retrovirus, preferably a lentivirus.

According to an embodiment, the nucleic acid sequence of the vector of step d) comprises a further nucleic acid sequence of interest.

According to an embodiment, the further nucleic acid of interest is selected from a nucleic acid encoding a chimeric antigen receptor (CAR), Mcl-1, Bcl-xL, and Helios.

According to an embodiment, the pluripotent stem cells are human induced pluripotent stem cells or human embryonic stem cells.

According to an embodiment, the method according to the invention further comprises a step of isolating T cells.

According to an embodiment, the method according to the invention further comprises a step of isolating a cell population selected from regulatory T cells (Treg), effector T lymphocytes (Teff), and CD4−CD8−CD3+TCRab+ T lymphocytes.

An object of the invention relates to a population of T cells obtainable according to the method of any one of the preceding claims.

According to an embodiment, the population of T cells according to the invention comprises CD8+CD3+TCRab+Foxp3+ and/or CD4+CD3+TCRab+Foxp3+ Treg cells, and/or CD8+ and/or CD4+ effector T cells, and/or CD8−CD4−CD3+TCRab+ T cells.

An object of the invention also relates to a population of T cells according to the invention for its use as a medicament.

Thus, the invention also relates to a population of CD8+CD3+TCRab+Foxp3+ and/or CD4+CD3+TCRab+Foxp3+ Treg cells, and/or CD8+ and/or CD4+ effector T cells, and/or CD4−CD8−CD3+TCRab+ T cells for use as a medicament.

Another object of the invention relates to a T cell population according to the invention for use in the treatment of a pathology related to an immune dysregulation such as infections, autoimmune diseases, inflammatory diseases, cancer, allergies, graft rejection, graft versus host disease.

The invention therefore further relates to a population of CD8+CD3+TCRab+Foxp3+ and/or CD4+CD3+TCRab+Foxp3+ Treg cells, and/or CD8+ and/or CD4+ effector T cells, and/or CD4−CD8−CD3+TCRab+ T cells for use in the treatment of a pathology related to an immune dysregulation such as infections, autoimmune diseases, inflammatory diseases, cancer, allergies, graft rejection, graft versus host disease.

In the context of the invention, the term "about" is used to indicate that a value comprises the variations inherent to the error margin related to the use of a measuring device, to the method used to determine the value, or variations that may exist between cells within the population studied and between populations. Thus, in an embodiment, the term "about", placed in front of a value, corresponds to ±10% of this value.

In the context of the invention, the terms "embryoid bodies" when referring to cells, designate three-dimensional structures or aggregates which comprise a population of pluripotent stem cells which have undergone differentiation. Methods of the art known to allow the development of embryoid bodies are for example described in WO2006021950 and Pettinato (Pettinato et al. 2015. Engineering Strategies for the Formation of Embryoid Bodies from Human Pluripotent Stem Cells. Stem Cells Dev. 24 (14): 1595-609).

In the context of the invention, the term "vector" refers to a macromolecule or to a complex of molecules comprising a polynucleotide to be delivered into a host cell. According to an embodiment, the vector is chosen from the group comprising the adenovirus vectors, plasmids, adeno-associated viral vectors, the retroviral vectors, the hybrid adeno-associated viral vectors, the lentivirus vectors, the herpes simplex viral vectors, the vaccines vectors, or a decorated pegylated liposome, carrying antibodies specific to the targeted host cell. According to an embodiment, the vector is a virus, particularly a retrovirus, more particularly a lentivirus. The term "plasmid" designates a common type of vector, which is an extrachromosomal DNA molecule separated from chromosomal DNA and which is capable of replicating independently of chromosomal DNA. In some cases, it is circular and double stranded.

In the context of the invention, the terms "gene", "polynucleotide", "coding region", "nucleic acid sequence", which encode a particular protein, is a nucleic acid molecule which is transcribed and optionally also translated into a gene product, e.g. a polypeptide. The coding region can be present either in the form of cDNA, genomic DNA, or RNA. When present in the form of a DNA, the nucleic acid molecule may be single-stranded (i.e. sense strand) or double stranded.

In the context of the invention, the term "transduction" is used to designate a mode of introduction of a vector comprising a nucleic acid sequence of interest into at least one cell of a "transduced" cell population. More particularly, the term "transduction" designates the introduction of a viral, preferably retroviral, preferably lentiviral, vector comprising a nucleic acid sequence of interest into at least one cell of a cell population.

In the context of the invention, the term "Foxp3" designates the Forkhead box P3 gene (official symbol FOXP3, ID: 50943 in humans), as well as the mRNA and the protein encoded by this gene. The protein expressed from this gene is a transcription factor belonging to the FOX protein family. It is also called scurfin.

In the context of the invention, the term "phenotype" designates the presence or absence of a particular marker, especially at the cell surface, or a set of cells within the population. For example, the "CD34+CD43+" phenotype designates a cell, or a set of cells in the population, which express CD34 and CD43. "CD43−" designates a cell, or a set of cells in the population, which does not express CD43. CD43, also known as Ly-48, leucosialin, sialophorin, leukocyte sialoglycoprotein, and W3/13, is a type I transmembrane glycoprotein comprising numerous O-glycosylation and sialylation sites. The phenotype can be identified by means known in the art. For example, an antibody specific for CD43 conjugated to allophycocyanin (APC) may be used to measure the expression of CD43 in a cell population by flow cytometry, and to identify the "CD43−" or "CD43+" phenotype. In another example, the "CD34+" phenotype may be identified by using an antibody specific for CD34 conjugated to the phycoerythrin-cyanine 7 (PE-Cy7) complex, which will bind to cells bearing the CD34 marker, and which can be quantified by flow cytometry. CD34, also called "gp105-120", is a transmembrane phosphoglycoprotein of about 105 to 120 kD, belonging to the sialomucin family.

In the context of the invention, the letter "D" followed by a number designates a particular day during the first phase of cell culture of the method of the invention (phase for obtaining embryoid bodies comprising hematopoietic stem cells). Thus, D0 corresponds to the start of the first phase, D1 is the day after D0 in the first phase, etc. The letters "Dd" followed by a number designate a particular day during the second phase of cell culture of the method of the invention (phase of differentiation into T cells). Thus, Dd0 is the start of the second phase, Dd1 is the day after Dd0 in the second phase, etc.

In the context of the invention, the term "treatment" designates the therapy, the prevention, the delay or the reduction of symptoms provoked by or caused by a pathology. In particular, the term "treatment" includes controlling the progression of the pathology and associated symptoms. The efficacy of the treatment of a pathology related to an immune dysregulation corresponds to a reduction in the unwanted immune response, or an increase in the deficient immune response. More generally, the treatment of a pathology related to an immune dysregulation enables to restore immune homeostasis (i.e. to reduce the intensity of the immune response when it is too strong, or increase the amplitude of the immune response when it is too low or null). The term "anti-rejection treatment" designates a treatment to prevent graft rejection (treatment of graft rejection). The term "anti-cancer treatment" designates a treatment for cancer.

DETAILED DESCRIPTION

Figure 1:
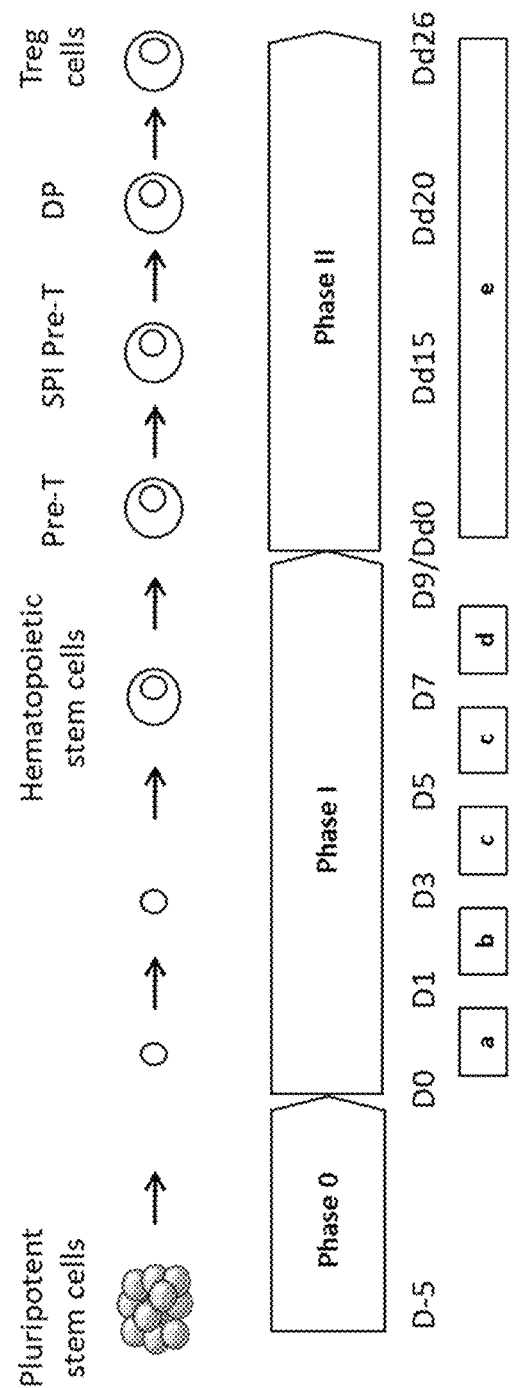
FIG. 1: schematic representation of the experimental protocol for cell differentiation according to a particular embodiment. The composition of the culture media is specified in the experimental part. Pre-T: prethymocytes; SPI Pre-T: single positive immature prethymocytes; DP: double positive thymocytes; Treg: regulatory T cells. The boxed letters a, b, c, d and e each correspond to a protocol for renewing the culture medium and/or reseeding the cells, details of which are given in the experimental part.

The inventors have discovered a new method for obtaining a population of T lymphocytes from pluripotent stem cells. More particularly, the population of T cells obtained according to the method of the invention may comprise CD8+CD3+TCRab+Foxp3+ and/or CD4+CD3+TCRab+Foxp3+ Treg cells, (Foxp3−) CD8+ and/or CD4+ Teff cells, and CD4−CD8−CD3+TCRab+ T cells.

The present invention relates to a method for obtaining a population of T cells from pluripotent stem cells, comprising the following steps:
 a) culturing pluripotent stem cells under conditions allowing to obtain embryoid bodies comprising at least 5% of CD34+CD43+ cells;
 b) dissociating said embryoid bodies;
 c) culturing said dissociated embryoid bodies with at least one Notch ligand, preferably in coculture with cells expressing at least one Notch ligand;
 d) optionally, carrying out, during step c), the introduction of a vector comprising at least one nucleic acid sequence encoding Foxp3 in at least one cell, preferably when at least 15% of the cell population exhibits the CD43− phenotype;
 said pluripotent stem cells not being human embryonic stem cells.

Another object of the invention relates to a method for obtaining a population of T cells from pluripotent stem cells, comprising the following steps:
 a) culturing pluripotent stem cells under conditions allowing to obtain embryoid bodies comprising at least 5% of CD34+CD43+ cells;
 b) dissociating said embryoid bodies;
 c) culturing said dissociated embryoid bodies with at least one Notch ligand, preferably in coculture with cells expressing at least one Notch ligand;
 d) carrying out, during step c), the introduction of a vector comprising at least one nucleic acid sequence encoding Foxp3 in at least one cell, preferably when at least 15% of the cell population exhibits the CD43− phenotype.

In an embodiment, the T cell population obtained by the method of the invention comprises regulatory T cells (Treg), effector T cells (Teff) and CD4−CD8−CD3+TCRab+ T cells.

According to an embodiment, the method according to the invention comprises two main steps of cell culture, separated by an intermediate step. The first main step allows to obtain hematopoietic stem cells from pluripotent stem cells, preferably said hematopoietic stem cells are comprised in an embryoid body. The intermediate step consists in dissociating the embryoid bodies. The second main step allows to obtain T cells from the hematopoietic stem cells obtained in step 1, and comprises the culture of said cells in the presence of at least one Notch ligand, for example with cells expressing at least one Notch ligand. Optionally, and more preferably concomitantly, this second step of differentiation into T lymphocytes also comprises the introduction of a vector comprising a nucleic acid sequence of interest into at least one cell.

The first step according to the invention allows to obtain hematopoietic stem cells from pluripotent stem cells.

Preferably, these pluripotent stem cells are pluripotent stem cells from mammals. Preferably, these pluripotent stem cells are human cells, preferably human induced pluripotent stem cells or human embryonic stem cells.

According to an embodiment, the pluripotent stem cells are human induced pluripotent stem cells.

The human induced pluripotent stem cells according to the invention can be obtained by reprogramming of differentiated cells, by methods known in the art, especially by the introduction of the Oct3/4, Sox2, c-Myc, and Klf4 genes by viral vectors, plasmids, Sendai viruses, or by injection of mRNA into cells. The differentiated cells may be, for example, skin fibroblasts, keratinocytes, adipocytes, hematopoietic cells.

Examples of human induced pluripotent stem cells comprise, without limitation, the hiPS T04 cells, the hiPS LON80 cells, hiPS LON71, hiPS BJ1, and hiPS MiPS.

According to an embodiment, the differentiated cells intended to be reprogrammed into induced pluripotent stem cells are from a biological sample taken from a subject. The biological sample can for example be chosen from a biopsy, a blood, plasma, serum, saliva sample, or a urine sample.

Thus, according to an embodiment of the invention, the method of the invention comprises a first step of obtaining induced pluripotent stem cells from differentiated cells taken from a subject.

According to an embodiment, the pluripotent stem cells are human embryonic stem cells.

Examples of human embryonic stem cells comprise, but are not limited to, hES WA09 cells, hES WA01 cells, hES WA07, hES BG01, hES and HUES7 cells.

According to a particular embodiment, pluripotent stem cells are embryonic stem cells which are not obtained by destruction of human embryos. Such method for obtaining such stem cells is in particular described by Chung et al. (2008).

According to another embodiment of the invention, the pluripotent stem cells are not human embryonic stem cells.

Before their differentiation into hematopoietic stem cells by the method of the invention, the pluripotent stem cells can be maintained in a culture medium suitable for their maintenance for several days to several weeks, and especially for about 1 to 10 days, in general for about 5 days after the last passage. Media suitable for maintaining pluripotent stem cells are known in the art. According to an embodiment, the culture medium for pluripotent stem cells comprises DMEM/F12 (Dulbecco's Modified Eagle Medium and nutrients, ThermoFisher).

Preferably, the culture medium for pluripotent stem cells comprises between about 5 and about 40%, preferably about 20% of KSR serum ("KnockOut Serum Replacement", ThermoFisher).

According to an embodiment, the culture medium for pluripotent stem cells comprises from about 0.1% to about 5% of L-glutamine, preferably about 1% of L-glutamine.

According to an embodiment, the culture medium for pluripotent stem cells comprises from about 0.1% to about 5% of non-essential amino acids, preferably about 1% of non-essential amino acids.

According to an embodiment, the culture medium for pluripotent stem cells comprises from about 0.01% to about 0.5% of 2-mercaptoethanol, preferably about 0.1% of 2-mercaptoethanol.

According to an embodiment, the culture medium for pluripotent stem cells comprises from about 1 to about 30 ng/mL of FGF2 (fibroblast growth factor 2, ThermoFisher), preferably about 10 ng/mL of FGF2.

According to an embodiment, the culture medium for pluripotent stem cells, preferably comprising DMEM/F12, comprises KSR serum, L-glutamine, non-essential amino acids, 2-mercaptoethanol and/or FGF2 as described above.

According to an embodiment, the culture medium for pluripotent stem cells, preferably comprising DMEM/F12, comprises KSR serum, L-glutamine, non-essential amino acids, 2-mercaptoethanol and FGF2 as described above.

According to an embodiment, the pluripotent stem cells are cultured in order to obtain hematopoietic stem cells.

Several culture conditions implemented to enable the appearance of hematopoietic stem cells are known in the art.

Thus, the first step of the method according to the invention (corresponding to step a) of the method according to the invention) consists in culturing pluripotent stem cells under conditions allowing to obtain embryoid bodies comprising at least 5% of CD34+CD43+ cells, preferably for at least 9 days.

According to a preferred embodiment, the pluripotent stem cells are cultured under conditions enabling to induce the formation of embryoid bodies. For this purpose, cell culture can be performed, for illustrative purposes, in a low-adhesion plate (Sigma-Aldrich, Fisher), which favors the appearance of cell aggregates in three dimensions (embryoid bodies) and reproduces in a more efficient way the intercellular interactions existing during the development of the embryo in the body of the animal.

In an embodiment, the culture of pluripotent stem cells in step a) is performed in a culture medium suitable to induce the formation of embryoid bodies, for at least 9 days, under conditions allowing to obtain embryoid bodies comprising at least 5% of CD34+CD43+ cells.

Culture media suitable for the growth of hematopoietic cells are known from the state of the art (see for example Chang et al. (2014)).

According to an embodiment, the culture medium to induce the formation of embryoid bodies comprises a serum-free culture medium suitable for the growth of hematopoietic cells, for example the StemPro-34 SFM medium (ThermoFisher).

According to an embodiment, the culture medium to induce the formation of embryoid bodies comprises from about 0.1 to about 5% of L-glutamine, preferably about 1% of L-glutamine.

According to an embodiment, the culture medium to induce the formation of embryoid bodies comprises from about 0.1 to about 5% of non-essential amino acids, preferably about 1% of non-essential amino acids.

According to an embodiment, the culture medium to induce the formation of embryoid bodies comprises from about 0.01 to about 0.5% of 2-mercaptoethanol, preferably about 0.1% of 2-mercaptoethanol.

According to an embodiment, the culture medium to induce the formation of embryoid bodies comprises from about 10 to about 1000 U/mL of penicillin, preferably about 100 U/mL of penicillin.

According to an embodiment, the culture medium to induce the formation of embryoid bodies comprises from about 10 to about 1000 ng/mL of streptomycin, preferably about 100 ng/mL of streptomycin.

According to an embodiment, the culture medium to induce the formation of embryoid bodies comprises from about 5 to about 1000 µg/mL, preferably about 50 µg/mL of ascorbic acid.

According to an embodiment, a serum-free culture medium suitable for the growth of hematopoietic cells, for example StemPro-34 SFM medium, comprises L-glutamine, non-essential amino acids, 2-mercaptoethanol, penicillin, streptomycin and/or ascorbic acid as described above.

In an embodiment, the culture of the pluripotent stem cells in step a) is carried out in a serum-free culture medium suitable for the growth of hematopoietic cells, for example StemPro-34 SFM medium (ThermoFisher), comprising BMP, FGF2, VEGF, SCF, Flt3-L and/or IL-3, for at least 9 days, under conditions allowing to obtain embryoid bodies comprising at least 5% of CD34+CD43+ cells.

In an embodiment, the culture of the pluripotent stem cells in step a) is carried out in a serum-free culture medium suitable for the growth of hematopoietic cells, for example StemPro-34 SFM medium (ThermoFisher), comprising BMP, FGF2, VEGF, SCF, Flt3-L and IL-3, for at least 9 days, under conditions allowing to obtain embryoid bodies comprising at least 5% of CD34+CD43+ cells.

According to a preferred embodiment, the pluripotent stem cells are first incubated in the presence of BMP (bone morphogenetic protein) to facilitate the induction of the formation of embryoid bodies. According to a preferred embodiment, the pluripotent stem cells are incubated for 10 to 48 hours, preferably for one day, in the presence of BMP. According to another embodiment, the cells are incubated in the presence of 3 to 300 ng/mL of BMP, preferably from 10 to 100 ng/mL of BMP, more preferably from 20 to 50 ng/mL of BMP, and particularly about 30 ng/mL of BMP. Preferably, the BMP is BMP-4, more preferably human BMP-4 (hBMP-4). More preferably, the cells are incubated for one day in the presence of about 30 ng/mL of hBMP-4a, preferably on D0 (start of the second phase).

In an embodiment, after the incubation in the presence of BMP, preferably BMP-4, a mixture comprising BMP (preferably BMP-4) and FGF-2 is added to the medium to allow induction of mesoderm.

Preferably between about 3 ng/mL and about 300 ng/mL of BMP, preferably BMP-4, and between about 0.5 ng/mL and about 50 ng/mL of FGF2 is added to the medium, preferably about 30 ng/mL of BMP, preferably BMP-4, and about 5 ng/mL of FGF2 are added to the medium. According to an embodiment, this addition is carried out all at once, preferably on day 1 of the phase of induction of the formation of embryoid bodies (day D1).

In an embodiment, a solution comprising growth factors and/or cytokines is added every two days, preferably from day 3 of the phase of induction of the formation of embryoid bodies (day D3), until the end of the induction phase of the formation of embryoid bodies.

The end of the induction phase of the formation of embryoid bodies corresponds to the moment when the embryoid bodies are dissociated. This can for example occur on day 5, day 6, day 7, day 8, day 9, day 10, day 11, day 12 of the induction phase of the formation of the embryoid bodies, or later (D5, D6, D7, D8, D9, D10, D11, D12 or later).

In a particular embodiment, step a) of culture of the pluripotent stem cells is carried out for at least 9 days.

The term "at least 9 days" includes 9 days, 10 days, 11 days or more. In an embodiment, step a) of culturing the pluripotent stem cells is thus carried out for 9 days.

In an embodiment, step a) is carried out for 9 to 17 days, preferably for 9 to 15 days, preferably for 9 to 14 days. In an embodiment, step a) is carried out for 9 to 12 days, preferably for 9 to 11 days, preferably for 9 to 10 days.

In an embodiment, the solution comprising growth factors and/or cytokines comprises VEGF (vascular endothelial growth factor, ThermoFisher), SCF (stem cell growth factor, ThermoFisher), FLt3-L (Fms-like tyrosine kinase 3-ligand, ThermoFisher), IL-3 (recombinant interleukin 3, ThermoFisher) and/or FGF2.

A preferred solution comprising growth factors and/or cytokines comprises VEGF (vascular endothelial growth factor, ThermoFisher), SCF (stem cell growth factor, ThermoFisher), FLt3-L (Fms-like tyrosine kinase 3-ligand, ThermoFisher), IL-3 (recombinant interleukin 3 ThermoFisher) and FGF2.

Preferably, the solution comprising growth factors and/or cytokines comprises from about 2 ng/mL to about 200 ng/mL VEGF, preferably about 20 ng/mL.

Preferably, the solution comprising growth factors and/or cytokines comprises from about 10 ng/mL to about 300 ng/mL of SCF, preferably about 100 ng/mL of SCF.

Preferably, the solution comprising growth factors and/or cytokines comprises from about 2 ng/mL to about 200 ng/mL of Flt3L, preferably about 20 ng/mL of Flt3L.

Preferably, the solution comprising growth factors and/or cytokines comprises from about 2 ng/mL to about 200 ng/mL of hIL-3, preferably about 20 ng/mL of hIL-3.

Preferably, the solution comprising growth factors and/or cytokines comprises from about 0.5 ng/mL to about 50 ng/mL of FGF2, preferably about 5 ng/mL of FGF2.

Preferably, a solution comprising growth factors and/or cytokines which does not comprise FGF2 is used just before the end of the phase of induction of the formation of embryoid bodies. Preferably, this solution is used from day D7 during the phase of induction of the formation of embryoid bodies.

According to an embodiment of the invention, the embryoid bodies obtained comprise hematopoietic stem cells capable of expressing the CD34 marker. Thus, the inventors have shown that the first step of the method of the invention allows to obtain a subpopulation of hematopoietic stem cells exhibiting the CD34+ phenotype. More particularly, about 40% of the total cell population expresses CD34+ after 7 days of culture (first phase). The inventors have further demonstrated the obtaining of a CD34+CD43+ subpopulation and a CD34+CD43-subpopulation, these two populations being present in relatively equivalent proportions in the population. Surprisingly, the inventors have shown that the increase of the CD34+CD43+ subpopulation in the embryoid bodies, and the presence of the CD34+CD43− subpopulation in the embryoid bodies, make the total cell population more suitable for continuing with the cell differentiation protocol according to the invention.

The inventors have shown that the conditions enabling to obtain embryoid bodies comprising at least 5% of CD34+CD43+ cells result from the nature of the culture medium, from the presence of the various factors and from the time of culture, these parameters being defined above.

In the context of the invention "at least 5%" includes 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 and 60%. In an embodiment, the culture conditions of step a) allow to obtain embryoid bodies comprising between about 5% and about 30, 40, 50 or 60% of CD34+CD43+ cells.

In an embodiment, the culture conditions of step a) allow to obtain embryoid bodies comprising at least 10% of CD34+CD43+ cells. In an embodiment, the culture conditions of step a) allow to obtain embryoid bodies comprising at least 15% of CD34+CD43+ cells.

In an embodiment, the culture conditions of step a) allow to obtain embryoid bodies comprising between about 5% and about 60% of CD34+CD43+ cells, preferably between about 10% and about 60% of CD34+CD43+ cells, preferably between about 15% and about 60% of CD34+CD43+ cells.

According to an embodiment, the method of the invention comprises the dissociation of the embryoid bodies (corresponding to step b) of the method of the invention, also called the intermediate step above), before their transfer into culture conditions allowing the differentiation of hematopoietic stem cells into T cells.

Embryoid bodies can be dissociated by methods known in the art. For example, embryoid bodies can be dissociated by enzymatic separation (trypsin, collagenase, dispase, etc.) or by mechanical separation.

According to an embodiment, the dissociation of the embryoid bodies is an enzymatic separation carried out by treatment with Accutase (Invitrogen).

According to an embodiment, the embryoid bodies are dissociated when at least 5%, preferably at least 10%, of the cell population exhibits the CD34+CD43+ phenotype.

According to an embodiment, the embryoid bodies are dissociated when at least 15% of the cell population exhibits the CD34+CD43+ phenotype. Preferably, the embryoid bodies are dissociated when at least 20% of the cell population exhibits the CD34+CD43+ phenotype.

According to an embodiment, the embryoid bodies are dissociated when at least 5, 6, 7, 8, 9, 10, 11, 12, 13, 14, 15, 16, 17, 18, 19, 20, 21, 22, 23, 24, 25, 26, 27, 28, 29 or 30% of the hematopoietic stem cell population exhibits the CD34+CD43+ phenotype.

Thus, in an embodiment, the dissociation of the embryoid bodies is carried out at the earliest on day 9 of culture for the differentiation of pluripotent stem cells into embryoid bodies ("D9").

According to an embodiment, the dissociation of the embryoid bodies is carried out between day 9 ("D9") and day 12 ("D12"), preferably between day 9 ("D9") and day 11 ("D11"), preferably between day 9 ("D9") and day 10 ("D10") of culture for the differentiation of pluripotent stem cells into embryoid bodies. According to an embodiment, the dissociation of the embryoid bodies is carried out on day 9 ("D9"), on day 10 ("D10"), or on day 11 ("D11") of culture for the differentiation of pluripotent stem cells into embryoid bodies. According to an embodiment, the dissociation of the embryoid bodies is performed on day 9 of culture for the differentiation of pluripotent stem cells into embryoid bodies ("D9").

Methods for measuring the expression of cellular markers are known in the art.

According to an embodiment, flow cytometry is used to measure the presence of markers in the cell population.

Antibodies which may be used to quantify CD34 are, for example, conjugated anti-CD34 antibodies, for example the CD34-PE-Cy7 antibody (Fisherscientific), or the CD34-APC antibody (BD Biosciences).

Antibodies which may be used to quantify CD43 are, for example, conjugated anti-CD43 antibodies, for example the CD43-APC antibody (Fisherscientific), the CD43eBioR2/60 antibody (Invitrogen), or the CD43-FITC antibody (Fisherscientific).

Known flow cytometry methods allow to count cells of interest, by placing them in suspension in a fluid stream and passing them through an electronic detection apparatus. Flow cytometry methods allow simultaneous multiparametric analyzes of physical and/or chemical parameters of several thousand particles per second, such as fluorescent parameters. Modern flow cytometry instruments typically have multiple lasers and fluorescence detectors.

Flow cytometry also allows to separate physically the cells in a heterogeneous mixture according to their properties, so as to isolate or purify the populations of interest. This method is known as "fluorescence activated cell sorting" or "FACS". According to this method, the initial complex cell mixture is first labeled with one or more antibodies specific for cell surface markers which have been conjugated to fluorescent dyes. Cells can also be analyzed that express one or more recombinant fluorescent proteins together with a gene of interest, allowing selection of cells without the use of antibodies.

Another method for sorting cell is Magnetic-activated cell sorting or "MACS". This method uses magnetic nanoparticles ("beads") coated with antibodies specific for certain cell surface markers. It is then possible to choose antibodies specific for either markers expressed by the population of interest (positive selection) or expressed by undesirable cell types (negative selection). After incubation of the nanoparticles with the cell population, the suspension is added to a special single-use separation column attached to a magnet to which the beads adhere, while unlabeled cells flow out.

According to an embodiment of the invention, the cells obtained after dissociation of the embryoid bodies are transferred to a second culture medium for the second step of cell culture of the method of the invention (corresponding to step c) of the method of the invention). The second step of cell culture of the method of the invention allows the differentiation of CD34+ hematopoietic stem cells from embryoid bodies into T cells.

According to an embodiment, all the cells resulting from the dissociation of the embryoid bodies are transferred to the culture conditions allowing the differentiation of the hematopoietic stem cells into T cells.

In an embodiment, dissociated embryoid bodies, obtained at the end of step b), are cultured in a culture medium of differentiation, preferably in a culture medium of differentiation comprising SCF, Flt3-L and IL-7, preferably for at least 15 days, with at least one Notch ligand, preferably in coculture with cells expressing at least one Notch ligand, so as to obtain said population of T cells.

According to an embodiment, the hematopoietic stem cells (i.e., cells exhibiting the CD34+ phenotype) derived from embryoid bodies are isolated and then placed under culture conditions allowing the differentiation of the hematopoietic stem cells into T cells.

Preferably, the differentiation into T cells is carried out in the presence of at least one Notch ligand (e.g. Delta-L1 or Delta-L4 ligands), preferably in the presence of a cell expressing at least one Notch ligand, even more preferably in the presence of a cell expressing at least one Notch ligand (examples: OP9-DLL1 or OP9-DLL4 or a mixture thereof). These cells are known in the art. In particular, the OP9-DLL1 and/or OP9-DLL4 cell lines can be used.

According to an embodiment, the culture medium for the differentiation into T cells comprises MEM (Minimum Essential Medium, Dutscher).

According to an embodiment, the culture medium for the differentiation into T cells comprises from about 2 to about 30% of FCS (Fetal Calf Serum), preferably about 20% of FCS.

According to an embodiment, the culture medium for the differentiation into T cells comprises from about 0.1 to about 5% of L-glutamine, preferably about 1% of L-glutamine.

According to an embodiment, the culture medium for differentiation into T cells comprises from about 0.1 to about 5% of non-essential amino acids, preferably about 1% of non-essential amino acids.

According to an embodiment, the culture medium for the differentiation into T cells comprises from about 0.01 to about 0.5% of 2-mercaptoethanol, preferably about 0.1% of 2-mercaptoethanol.

According to an embodiment, the culture medium for the differentiation into T cells comprises from about 5 to about 1000 µg/mL, preferably about 10 to 100 µg/mL of ascorbic acid, more particularly about 50 µg/mL of ascorbic acid.

According to an embodiment, the culture medium for the differentiation into T cells, preferably comprising MEM (Minimum Essential Media, Dutscher) comprises FCS, L-glutamine, non-essential amino acids, 2-mercaptoethanol and/or ascorbic acid as described above. In an embodiment, during the phase of differentiation of T cells (second phase), a solution comprising growth factors and/or cytokines is added in the medium. In an embodiment, the solution comprising growth factors and/or cytokines comprises SCF (stem cell growth factor), FLt3-L (Fms-like tyrosine kinase 3 ligand), and/or IL-7 (interleukin 7).

Preferably, the preferred solution comprising growth factors and/or cytokines comprises SCF (stem cell growth factor), FLt3-L (Fms-like tyrosine kinase 3 ligand), and IL-7 (interleukin 7).

Preferably, the solution comprising growth factors and/or cytokines comprises from about 5 ng/mL to about 300 ng/mL of SCF, preferably from about 5 ng/mL to about 50 ng/mL of SCF, more particularly about 10 ng/mL of SCF.

Preferably, the solution comprising growth factors and/or cytokines comprises from about 2 ng/mL to about 200 ng/mL of Flt3L, preferably about 5 ng/mL to about 50 ng/mL of Flt3L, more particularly about 10 ng/mL of Flt3L.

Preferably, the solution comprising growth factors and/or cytokines comprises from about 2 ng/mL to about 200 ng/mL of IL-7 (interleukin 7, Gibco), preferably about 2 ng/mL to about 50 ng/mL of IL-7, particularly about 5 ng/mL of IL-7.

According to an embodiment, the solution comprising growth factors and/or cytokines is added to the medium every one, two or three days, preferably every two days, during the phase of differentiation into T cells (second phase).

According to an embodiment, the cells are transferred to a new culture medium for differentiation into T cells in the presence of at least one Notch ligand, for example in the presence of cells expressing at least one Notch ligand, every 3, 4, 5 or 6 days, preferably every 5 days, from the start of the T cell differentiation phase.

According to an embodiment, the phase of differentiation into T cells lasts at least 7 days, preferably at least 10 days, preferably at least 15 days, preferably at least 20 days, preferably at least 25 days. According to an embodiment, the phase of differentiation into T cells lasts about 26 days.

According to an embodiment, the method according to the invention further comprises introducing a vector comprising a nucleic acid sequence of interest (corresponding to step d) of the method of the invention). Preferably, this nucleic acid sequence encodes Foxp3. According to an embodiment, the vector further comprises the nucleic acid sequence of at least another gene, or encoding at least one other mRNA of interest, possibly translated into a further polypeptide of interest. Examples of such nucleic acid sequences of interest include, without limitation, a nucleic acid sequence encoding a chimeric antigen receptor (CAR), a nucleic acid sequence encoding Mcl-1, a nucleic acid sequence encoding Bcl-xL, and a nucleic acid sequence encoding Helios.

According to an embodiment, step d) of introducing a vector comprising a nucleic acid sequence of interest, preferably a nucleic acid sequence encoding Foxp3, is performed between day Dd8 and day Dd12, preferably between day Dd9 and day Dd11, of step c), i.e. of the phase of differentiation into T cells. According to an embodiment, step d) of introducing a vector comprising a nucleic acid sequence of interest, preferably a nucleic acid sequence encoding Foxp3, is carried out on day Dd9, on day Dd10 or on day Dd11 of the T cells differentiation phase (second main phase of cell culture, corresponding to step c) of the method of the invention).

The term "Dd" indicates the number of days of the T cells differentiation phase, i.e. of the second phase of cell culture.

Preferably, the introduction of a vector comprising a nucleic acid sequence of interest, preferably a nucleic acid sequence encoding Foxp3, is carried out at day Dd10 of the second phase of cell culture, i.e. during step c) of the method of the present invention. More preferably, the introduction of a vector comprising a nucleic acid sequence of interest, preferably a nucleic acid sequence encoding Foxp3, is carried out on the $10^{th}$ day after bringing together the cells with at least one Notch ligand.

Indeed, surprisingly, the inventors have shown that the cell phenotypes observed on day 26 of the second phase ("Dd26") were particularly improved when the transduction had been carried out on day Dd10 of the second phase of cell culture. Indeed, cells observed on day Dd26 of the second phase comprise a greater proportion of cells expressing CD3 and TCR when the transduction was performed on day Dd10 of the second phase of cell culture. The inventors have moreover characterized the expression of several markers for the cells on days 8, 10 and 12 after bringing together at least one Notch ligand. In this way, they have shown, in particular, a decrease in the expression of CD43 on day Dd10 of the second phase, with respect to days Dd8 and Dd12. Without wishing to be bound by any theory, the inventors suggest that an increase in the proportion of cells exhibiting the CD43− phenotype in the cell population could be associated with a greater efficiency of the introduction of a vector comprising a nucleic acid sequence of interest.

Thus, according to an embodiment, the introduction of a vector comprising a nucleic acid sequence of interest is performed when at least 15% of the cell population exhibits the CD43-phenotype. Preferably, the introduction of a vector comprising a nucleic acid sequence of interest is carried out when at least 20% of the cell population exhibits the CD43− phenotype. More preferably, the introduction of a vector comprising a nucleic acid sequence of interest is carried out when at least 25% of the cell population exhibits the CD43− phenotype.

According to an embodiment, the introduction of a vector comprising a nucleic acid sequence of interest is performed when 15% to 40% of the cell population exhibits the CD43− phenotype.

It is understood that "from 15% to 40%" includes 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% and 40%.

According to an embodiment of the invention, the method for obtaining a population of T cells from pluripotent stem cells comprises the following steps:
 a) culturing pluripotent stem cells in a serum-free culture medium suitable for the growth of hematopoietic cells, comprising BMP, FGF2, VEGF, SCF, Flt3-L and IL-3, for at least 9 days, under conditions allowing to obtain embryoid bodies comprising at least 5% of CD34+ CD43+ cells;
 b) dissociating said embryoid bodies;
 c) culturing said dissociated embryoid bodies in a differentiation culture medium comprising SCF, Flt3-L, and IL-7, for at least 15 days, with at least one Notch ligand, preferably in coculture with cells expressing at least one Notch ligand, so as to obtain said population of T cells;
 d) carrying out, during step c), the introduction between day 8 (Dd8) and day 12 (Dd12) of a vector comprising at least one nucleic acid sequence encoding Foxp3 in at least one cell, preferably when at least 15% of the cell population exhibits the CD43− phenotype.

According to an embodiment of the invention, the vector comprises a nucleic acid sequence encoding only Foxp3.

According to another embodiment, the introduced vector further comprises another nucleic acid sequence. This additional sequence may for example correspond to the gene encoding Mcl-1 and is described, for example, in application WO2014180943. The additional sequence may also correspond to the gene encoding Bcl-xL as described in Haque et al. (2012). The additional sequence may also correspond to the gene encoding Helios (zinc finger protein) as described in Baine et al. (2013).

According to an particular embodiment, the further nucleic acid sequence is a nucleic acid sequence encoding a chimeric antigen receptor (CAR). According to an embodiment, the chimeric antigen receptor (CAR) is an anti-HLA CAR, namely a CAR targeting or recognizing an HLA antigen, preferably chosen from the group consisting of HLA-A, HLA-B, HLA-C, HLA-E, HLA-F, HLA-G, HLA-DM, HLA-DO, HLA-DP, HLA-DQ, and HLA-DR. Thus, according to an embodiment, the additional nucleic acid sequence is a nucleic acid sequence encoding an anti-HLA-A2 chimeric antigen receptor (CAR) (i.e. a CAR targeting or recognizing HLA-A2), as described in MacDonald et al. (2016).

CARs are artificial receptors constituted of a targeting domain associated with one or more intracellular signaling domain(s), generally via a transmembrane domain CARs are designed to recognize an antigen present on the surface of cells to be targeted, for example immune cells to be suppressed in the context of an anti-rejection treatment or tumor cells in the context of an anti-cancer treatment.

In general, the targeting domain of a CAR is a single-chain variable fragment of an antibody (scFv). Targeting domains derived from binding domains from receptors or ligands have also been used with success. The intracellular signaling domain of first-generation CARs is a stimulation domain generally derived from CD3zeta. Second and third-generation CARs further comprise one (second-generation CAR) or more (third-generation CAR) intracellular signaling domains derived from co-stimulatory molecules, such as CD28, OX-40 (CD134), and 4-1BB (CD137).

Strategies to conceptualize and produce chimeric antigen receptors (CARs) are well known in the state of the art. By way of illustration, the following references can be cited: Bonini and Mondino (2015), Srivastava and Riddell (2015), Jensen and Riddell (2015), and Gill and June (2015).

The skilled person in the art is able to identify genes of interest which could be used alone or in combination with the nucleic acid sequence encoding Foxp3 gene.

According to an embodiment, the vector is chosen from the group comprising adenovirus vectors, plasmids, adeno-associated viral vectors, retroviral vectors, hybrid adeno-associated viral vectors, lentivirus vectors, herpes simplex viral vectors, vaccines vectors, or a decorated pegylated liposome, carrying antibodies specific for the target cell. According to an embodiment, the vector is a retrovirus, preferably a lentivirus.

According to an embodiment, expression of the nucleic acid of interest involves the Crispr-Cas9 system.

According to an embodiment of the invention, at the end of the second phase of cell culture of the method according to the invention, the cell population in culture comprises Treg cells. According to an embodiment of the invention, at the end of the second phase of cell culture of the method according to the invention, the cell population in culture comprises Treg cells and/or Teff cells. According to an embodiment of the invention, at the end of the second phase of cell culture of the method according to the invention, the cell population in culture comprises Treg cells, Teff cells and/or CD4−CD8−CD3+TCRab+ T cells.

According to an embodiment of the invention, at the end of the second phase of cell culture of the method according to the invention, the cell population in culture comprises Treg and Teff cells and CD4−CD8−CD3+TCRab+ T cells.

According to an embodiment, the method of the invention further comprises a step of isolation and/or purification of T cells, wherein the T cells may be isolated from the medium by known techniques. For example, the FACS or MACS methods which are described above enable to isolate and purify a population of T cells.

According to another embodiment, the method of the invention further comprises a step of isolation and/or purification of Treg cells. For example, the FACS or MACS methods which are described above enable to isolate and purify a population of Treg cells, for example Dynabeads Regulatory CD4+/CD25+ TCell Kit (Invitrogen).

According to an embodiment, the method of the invention further comprises a step of isolation and/or purification of Teff cells. For example, the FACS or MACS methods which are described above enable to isolate and purify a population of Teff cells. For this, cells can be identified by the use of anti-CD4, anti-CD8, anti-TCRab markers, and expression of Foxp3. Those which express CD4 and/or CD8 and/or TCR but which do not express Foxp3 can be considered as effector T cells.

According to another embodiment, the method of the invention further comprises a step of isolation and/or purification of CD4−CD8−CD3+TCRab+ T cells. For example, the FACS or MACS methods which are described above enable to isolate and purify a population of CD4−CD8−CD3+TCRab+ T cells.

According to an embodiment, the method of the invention further comprises a step of transducing T cells, in particular Treg cells, Teff cells and/or CD4−CD8−CD3+TCRab+ T cells, with a nucleic acid sequence encoding a chimeric antigen receptor ("CAR"), for example an anti-HLA CAR, and more particularly an anti-HLA-A2 CAR, as described above, so as to obtain T cells according to the invention expressing a CAR, for example an anti-HLA CAR, and more particularly an anti-HLA-A2 CAR. This transduction can be carried out according to methods known in the art. For example, transduction can be performed by ex vivo gene transfer through the use of a retrovirus or lentivirus comprising a nucleic acid sequence encoding the CAR.

The invention relates to a method for obtaining a population of T cells from pluripotent stem cells, comprising the following steps:
  (a) culturing pluripotent stem cells under conditions allowing the obtaining of hematopoietic stem cells;
  b) placing said hematopoietic stem cells under conditions allowing their differentiation into T cells;
  c) optionally or concomitantly carrying out, during step b), the introduction of a vector comprising a nucleic acid sequence of interest into at least one cell.

According to an embodiment, the invention relates to a method for obtaining a population of T cells from pluripotent stem cells, comprising the following steps:
  a) culturing pluripotent stem cells under conditions allowing the obtaining of hematopoietic stem cells;
  b) placing said hematopoietic stem cells under conditions allowing their differentiation into T cells;
  c) carrying out, during step b), the introduction of a vector comprising a nucleic acid sequence of interest into at least one cell.

According to an embodiment, the cells are transferred and step b) begins when at least 5% of the cell population exhibits the CD34+CD43+ phenotype. According to an embodiment, the cells are transferred and step b) begins when at least 10% of the cell population exhibits the CD34+CD43+ phenotype. According to an embodiment, the cells are transferred and step b) begins when at least 15% of the cell population exhibits the CD34+CD43+ phenotype.

According to an embodiment, the introduction of a vector planned at step c) is carried out when at least 15% of the cell population exhibits the CD43− phenotype.

According to an embodiment, the introduction of a vector planned at step c) is carried out between day 8 (Dd8) and day 12 (Dd12) of the second phase of cell culture allowing the differentiation of the hematopoietic stem cells into T cells. According to an embodiment, the introduction of a vector planned at step c) is carried out between day 9 (Dd9) and day 11 (Dd11) of the second phase of cell culture allowing the differentiation of the hematopoietic stem cells into T cells. According to an embodiment, the introduction of a vector planned at step c) is carried out on day 9 (Dd9), on day 10 (Dd10) or on day 11 (Dd11), preferably on day 10 (Dd10) of the second phase of cell culture allowing the differentiation of the hematopoietic stem cells into T cells.

According to an embodiment, the method of the invention comprises the following steps:
  a) culturing pluripotent stem cells under conditions enabling to obtain embryoid bodies comprising at least 5% of CD34+CD43+ cells;
  b) dissociating said embryoid bodies;
  c) placing said dissociated embryoid bodies in the presence of at least one Notch ligand, preferably for at least 15 days;
  d) optionally or concomitantly, carrying out, during step c), the introduction, preferably between day 8 (Dd8) and day 12 (Dd12), of a vector comprising at least one nucleic acid sequence encoding Foxp3 in at least one cell, preferably when at least 15% of the cell population exhibits the CD43− phenotype.

According to an embodiment, the method of the invention comprises the following steps:
  a) culturing pluripotent stem cells under conditions enabling to obtain embryoid bodies comprising at least 5% of CD34+CD43+ cells;
  b) dissociating said embryoid bodies;
  c) placing said dissociated embryoid bodies in the presence of at least one Notch ligand, preferably for at least 15 days;
  d) carrying out, during step c), the introduction, preferably between day 8 (Dd8) and day 12 (Dd12), preferably between day 9 (Dd9) and day 11 (Dd11), of a vector comprising at least one nucleic acid sequence encoding Foxp3 in at least one cell, preferably when at least 15% of the cell population exhibits the CD43− phenotype.

According to a preferred embodiment, the invention relates to a method for obtaining a population of T cells from pluripotent stem cells, comprising the following steps:
  a) culturing pluripotent stem cells under conditions enabling to obtain hematopoietic stem cells, comprising the development of embryoid bodies, then dissociating said embryoid bodies;

b) placing said dissociated embryoid bodies comprising the hematopoietic stem cells in the presence of at least one Notch ligand, preferably for at least 15 days, for example in coculture with cells expressing at least one Notch ligand, to allow their differentiation into T cells;
c) optionally or concomitantly carrying out, during step b), the introduction, preferably between day 8 (Dd8) and day 12 (Dd12), of a vector comprising at least one nucleic acid sequence encoding Foxp3 in at least one cell;

preferably wherein the cells are placed in the presence of at least one Notch ligand according to step b) when at least 5% of the cell population exhibits the CD34+CD43+ phenotype, and preferably wherein the introduction of a vector planned at step c) is performed when at least 15% of the cell population exhibits the CD43− phenotype.

According to another preferred embodiment, the invention relates to a method for obtaining a population of T cells from pluripotent stem cells, comprising the following steps:
a) culturing pluripotent stem cells under conditions enabling to obtain hematopoietic stem cells, comprising the development of embryoid bodies, then dissociating said embryoid bodies;
b) placing said dissociated embryoid bodies comprising the hematopoietic stem cells in the presence of at least one Notch ligand, preferably for at least 15 days, for example in coculture with cells expressing at least one Notch ligand, to allow their differentiation into T cells;
c) carrying out, during step b), the introduction, preferably between day 8 (Dd8) and day 12 (Dd12), preferably between day 9 (Dd9) and day 11 (Dd11), of a vector comprising at least one nucleic acid sequence encoding Foxp3 in at least one cell;

preferably wherein the cells are placed in the presence of at least one Notch ligand according to step b) when at least 5% of the cell population exhibits the CD34+CD43+ phenotype, and preferably wherein the introduction of a vector planned at step c) is performed when at least 15% of the cell population exhibits the CD43− phenotype.

According to another preferred embodiment, the invention relates to a method for obtaining a population of T cells from pluripotent stem cells, comprising the following steps:
a) culturing pluripotent stem cells under conditions enabling to obtain hematopoietic stem cells, comprising the development of embryoid bodies, then dissociating said embryoid bodies;
b) placing said dissociated embryoid bodies comprising the hematopoietic stem cells in the presence of at least one Notch ligand, preferably for at least 15 days, for example in coculture with cells expressing at least one Notch ligand, to allow their differentiation into T cells;
c) carrying out, during step b), the introduction, preferably between day 8 (Dd8) and day 12 (Dd12), of a vector comprising at least one nucleic acid sequence encoding Foxp3 into at least one cell;

characterized in that the cells are placed in the presence of at least one Notch ligand according to step b) when at least 5%, preferably at least 10%, preferably at least 15%, of the cell population exhibits the CD34+CD43+ phenotype, and in that the introduction of a vector planned in step c) is carried out when at least 15%, preferably at least 20%, of the cell population exhibits the CD43− phenotype.

The invention also relates to a method for obtaining T cells from hematopoietic stem cells comprising introducing a nucleic acid sequence into at least one cell of a population of hematopoietic stem cells, when at least 15%, preferably at least 20% of said population exhibits the CD43− phenotype. Preferably, the invention relates to a method for obtaining T cells from hematopoietic stem cells comprising the introduction of a nucleic acid sequence encoding Foxp3 into at least one cell of a population of hematopoietic stem cells, when at least 15%, preferably at least 20% of said population exhibits the CD43− phenotype.

According to an embodiment, the method according to the invention allows to obtain a population of T cells comprising Tregs, and/or Teffs, and/or CD4−CD8−CD3+TCRab+ T cells.

According to an embodiment, the method according to the invention allows to obtain a population of T cells comprising CD8+CD3+TCRab+Foxp3+ and/or CD4+CD3+TCRab+Foxp3+ Tregs, CD8+ and/or CD4+ effector T cells, and CD4−CD8−CD3+TCRab+ T cells.

According to an embodiment, the method according to the invention allows to obtain a population of T cells comprising CD8+CD3+TCRab+Foxp3+ and CD4+CD3+TCRab+Foxp3+ Tregs, CD8+ and CD4+ effector T cells, and CD4−CD8−CD3+TCRab+ T cells.

The present invention therefore also relates to a population of T cells comprising Tregs, and/or Teffs, and/or CD4−CD8−CD3+TCRab+ T cells.

According to an embodiment, the population of T cells comprises CD8+CD3+TCRab+Foxp3+ and/or CD4+CD3+TCRab+Foxp3+ Tregs, CD8+ and/or CD4+ effector T cells, and CD4−CD8−CD3+TCRab+ T cells.

According to an embodiment, the population of T cells comprises CD8+CD3+TCRab+Foxp3+ and CD4+CD3+TCRab+Foxp3+ Treg cells, CD8+ and CD4+ effector T cells, and CD4−CD8−CD3+TCRab+ T cells.

Methods such as FACS or MACS enable to isolate certain particular populations such as the population consisting of Treg cells, the population consisting of Teff cells, or the population consisting of CD4−CD8−CD3+TCRab+ T cells, or combinations thereof. Such methods also enable to isolate subpopulations such as the subpopulation of CD8+CD3+TCRab+Foxp3+ Treg cells, the subpopulation consisting of CD4+CD3+TCRab+Foxp3+ Treg cells, the subpopulation consisting of CD8+ effector T cells, the subpopulation consisting of CD4+ effector T cells or the subpopulation consisting of CD4−CD8−CD3+TCRab+ T cells.

The person skilled in the art is capable of identifying and applying other methods known from the state of the art enabling to isolate such populations and cell sub-populations.

An object according to the invention also relates to the populations of T cells obtained or obtainable by the method of the invention.

According to an embodiment, the population is a Treg population, exhibiting the following phenotype: CD8+CD3+TCRab+Foxp3+ and/or CD4+CD3+TCRab+Foxp3+. According to another embodiment, the population is a CD4+ and/or CD8+ Teff population. According to another embodiment, the population is a CD4−CD8−CD3+TCRab+ population. According to an embodiment, the population consists of Treg, and/or Teff, and/or CD4−CD8−CD3+TCRab+ T cells.

According to an embodiment, the T cells obtainable by the method according to the invention are then transformed (or transduced) to allow the expression of a chimeric antigen receptor ("CAR"), for example an anti-HLA CAR, and more particularly an anti-HLA-A2 CAR, as described above. This transformation (or transduction) may be carried out according to methods known in the art. For example, transformation (or transduction) may be carried out by ex vivo gene transfer using a retrovirus or lentivirus comprising a nucleic acid sequence encoding the CAR.

According to another embodiment, the T cells obtainable by the method according to the invention are then amplified. For example, T cells may be amplified by inducing their proliferation in a polyclonal fashion in the presence of anti-CD3 and anti-CD28 monoclonal antibodies. Methods of T cell expansion are known in the art, for example in Petersen (Petersen et al. 2018 "Improving T-Cell Expansion and Function for Adoptive T-Cell Therapy Using Ex Vivo Treatment with PI3Kδ Inhibitors and VIP Antagonists." Blood Advances 2.3: 210-223) or Boursier (Boursier et al. 2012 "Utilisation des lymphocytes T régulateurs en thérapies cellulaires dans les maladies auto-immunes." Medicine/Science 28: 757-63).

A further object of the invention is a T cell population as described above for use as a medicament.

Preferably, the invention relates to a population of T cells for use in cell therapy. In particular, the population of T cells can be used in personalized medicine, for example differentiated cells can be taken from a patient, then reprogrammed into human induced pluripotent stem cells and used according to the method of the invention to provide new T cells, which can be administered to said patient.

Another object according to the invention is a population of T cells as described above for use in the treatment of a pathology related to an immune dysregulation.

In the context of the invention, a pathology related to immune dysregulation comprises pathologies wherein the immune response is deteriorated (e.g., it does not occur or is reduced) and does not allow to fight effectively against the pathogen, and pathologies wherein the immune response is too strong and causes, for example, damages to self-cells. Such pathologies correspond, among others, to infections, autoimmune diseases, inflammatory diseases, cancers, allergies, graft rejection, or graft versus host disease.

According to an embodiment of the invention, a therapeutically effective amount of T cells according to the invention is to be administered to the subject to be treated.

A therapeutically effective amount of T cells according to the invention includes, for example, an amount which is effective for restoring immune homeostasis, i.e. reducing the intensity of the immune response when it is too strong, or increasing the amplitude of the immune response when it is too weak or null.

According to an embodiment, the population of T cells is a population of Treg cells. According to a preferred embodiment, the T cell population is a Treg cell population for use in the treatment of graft rejection, graft versus host disease, autoimmune diseases and inflammatory diseases. According to a particulier embodiment, the T cell population is a Treg cell population expressing a chimeric antigen receptor (CAR), for example an anti-HLA CAR, more particularly an anti-HLA-A2 CAR, for use in anti-rejection treatment or a treatment for graft versus host disease.

According to an embodiment, the population of T cells is a population of Teff cells and/or of CD4−CD8−CD3+TCRab+ T cells. According to a preferred embodiment, the population of T cells is a population of Teff cells and/or of CD4−CD8−CD3+TCRab+ T cells for use in the treatment of cancers or infections. According to a particular embodiment, the T cell population is a population of Teff cells and/or CD4−CD8−CD3+TCRab+ T cells expressing a chimeric antigen receptor (CAR) for use in the treatment of cancers. An object of the invention relates to a method for modulating the immune system comprising the administration to a subject to be treated of a population of T cells as described above, preferably obtained by the method of the invention as described above.

According to an embodiment, the invention relates to a method of modulating the immune system by cell therapy comprising the administration to a subject to be treated of a population of T cells as described above, preferably obtained by the method of the invention as described above.

According to an embodiment, the method of modulating the immune system as described above comprises the administration to a subject to be treated of a therapeutically effective amount of T cells according to the invention, preferably obtained by the method of the invention as described above.

An object of the invention relates to a method of treatment of a pathology related to an immune dysregulation comprising the administration to a subject to be treated of a population of T cells as described above, preferably obtained by the method of the invention as described above.

According to an embodiment, the method is a method of treatment of a graft rejection, graft versus host disease, an autoimmune disease or an inflammatory disease and it preferably comprises the administration to a subject to be treated of a population of Treg cells as described above. According to an embodiment, the Treg cells express a chimeric antigen receptor (CAR), for example an anti-HLA CAR, and more particularly an anti-HLA-A2 CAR. Thus, in an embodiment, the method is a method of treatment of a graft rejection or graft versus host disease, and it comprises the administration to a subject to be treated a population of Treg cells expressing a chimeric antigen receptor (CAR), for example an anti-HLA CAR, and more particularly an anti-HLA-A2 CAR.

According to an embodiment, the method is a method of treatment of a cancer or an infection and it preferably comprises the administration to a subject to be treated of a population of Teff cells and/or CD4−CD8−CD3+TCRab+ T cells as described above. According to an embodiment, the Teff cells and/or CD4−CD8−CD3+TCRab+ T cells express a chimeric antigen receptor (CAR). Thus, in an embodiment, the method is a method of treatment of a cancer and it comprises the administration to a subject to be treated of a population of Teff cells and/or CD4−CD8−CD3+TCRab+ T cells expressing a chimeric antigen receptor (CAR).

According to an embodiment, the method of treatment according to the invention comprises the administration to a subject to be treated of a therapeutically effective amount of T cells according to the invention, preferably obtained by the method of the invention as described above.

An object of the invention relates to the use of a population of T cells according to the invention, preferably obtained by the method of the invention, for the manufacture of a medicament for the treatment of a pathology related to an immune dysregulation.

According to an embodiment, the T cell population is a population of Treg cells as described above and the medicament is for the treatment of a graft rejection, graft versus host disease, an autoimmune disease or inflammatory disease. According to an embodiment, the Treg cells express a chimeric antigen receptor (CAR), for example an anti-HLA CAR, and more particularly an anti-HLA-A2 CAR. Thus, according to an embodiment, the population of T cells is a population of Treg cells expressing a chimeric antigen receptor (CAR), for example an anti-HLA CAR, and more particularly an anti-HLA-A2 CAR, and the medicament is for the treatment of a graft rejection or graft versus host disease.

According to an embodiment, the T cell population is a population of Teff cells and/or CD4−CD8−CD3+TCRab+ T cells as described above and the medicament is for the treatment of a cancer or an infection. According to an embodiment, the Teff cells and/or CD4−CD8−CD3+ TCRab+ T cells express a chimeric antigen receptor (CAR). Thus, according to an embodiment, the population of T cells is a population of Teff cells and/or CD4−CD8−CD3+ TCRab+ T cells expressing a chimeric antigen receptor (CAR) and the medicament is for the treatment of a cancer.

An object of the invention relates to a kit for use in the method according to the invention, comprising a culture plate for the formation of embryoid bodies comprising hematopoietic stem cells, a culture medium for inducing the formation of embryoid bodies, a culture plate for the differentiation of hematopoietic stem cells into T cells, a culture medium for the differentiation into T cells and solutions comprising growth factors and/or cytokines, as defined above.

EXAMPLES

Example 1 (Reference Example Illustrating the Implementation of the Method of the Invention)

Experimental Protocol

The research protocol was conducted in compliance with French legal guidelines and the ethics committee of local institutions.

Pluripotent Stem Cells

The undifferentiated colonies of human pluripotent stem cells (commercial hES WA09 (WiCell) line) were maintained in culture on mouse embryonic fibroblasts ("MEF") in a medium for pluripotent stem cells comprising DMEM/F12, 20% KSR ("KnockOut serum replacement") serum, 1% L-glutamine, 1% non-essential amino acids, 0.1% 2-mercaptoethanol, 10 ng/mL FGF2 (fibroblast growth factor) (FIG. 1, "Phase 0"). A passage is carried out every 5 to 6 days.

Method of Obtaining Hematopoietic Stem Cells (Phase I)

For the differentiation of human pluripotent stem cells in hematopoietic cells, undifferentiated colonies were treated with dispase (1 U/mL) for 10 minutes and transferred to low adherence plates to allow the formation of embryoid bodies. The culture medium used for this step (FIG. 1, "phase I") consists of STemPro-34 (ThermoFisher), 1% L-glutamine, 1% non-essential amino acids, 0.1% 2-mercaptoethanol, 100 U/mL penicillin and 100 ng/mL streptomycin and 50 µg/mL ascorbic acid.

The formation of the embryoid bodies was facilitated by an incubation for one day in the presence of 30 ng/mL of hBMP-4 ("human bone morphogenetic protein 4") (FIG. 1, letter "a").

The embryoid bodies were then cultured with 30 ng/mL of BMP-4 and 5 ng/mL of FGF2 until day D3 (FIG. 1, letter "b") to enable mesoderm induction.

Between days D3 and D5, and then D5 and D7, the speciation and the growth continues in the presence of hVEGF (20 ng/mL) and a cocktail of growth factors and hematopoietic cytokines (hSCF at 100 ng/mL, hFlt3-L at 20 ng/mL, hIL-3 at 20 ng/mL and FGF2 at 5 ng/mL) (FIG. 1, letter "c").

Then, the differentiation is continued from D7 to D9 with the same cytokines but without FGF2 (FIG. 1, letter "d").

Determination of Embryoid Bodies Cell Phenotypes at D7, D8 and D9

The embryoid bodies at D7, D8 and D9, containing the hematopoietic stem cells, were dissociated by treatment with Accutase® for 10 minutes and the markers present were analyzed by flow cytometry.

Method for Obtaining T Cells (Phase II)

The embryoid bodies obtained at D9 were dissociated by treatment with Accutase® for 10 minutes. The cells thus isolated were seeded on monolayers of OP9-DLL1 cells to allow their differentiation into lymphoid T. The culture medium "middle OP9" (FIG. 1, "Phase II") enabling this differentiation comprises: α-MEM with 20% FBS, 1% L-glutamine, 1% non-essential amino acids, 0.1% 2-mercaptoethanol, 100 U/mL penicillin, 100 ng/mL streptomycin and 50 µg/mL ascorbic acid, supplemented with SCF (10 ng/mL), IL-7 (5 ng/mL) and Flt3L (5 ng/mL). Every two days, half of the medium was replaced and every 5 days the cells were transferred to new OP9-DLL1 monolayers (FIG. 1, letter "e").

Lentivirus Production and Titration

A DNA plasmid was created which comprises 9 µg of lentivirus carrying the construct pMSCV-Human Foxp3-EF1-GFP-T2A-Puro (FOXP3GFP), 8 µg of packaging plasmid psPAX2 and 4 µg of plasmid pMD2G. It was transfected into HEK293T cells using the calcium chloride method. Lentiviral particles were collected between 42 and 66 hours after transfection in the supernatant of HEK293T cells. For titration, 100,000 Jurkat cells were cultured and contaminated with a serial dilution of half of the viruses ranging from 10 µL to 0.078 µL. Three days later, the cells were harvested and the fluorescence of the GFP (Green Fluorescent Protein) was analyzed by flow cytometry.

Transduction of Cells Undergoing Differentiation

The cells of Dd0, Dd5, Dd10 and Dd15 (respectively on the $5^{th}$, $10^{th}$, and $15^{th}$ day after the start of culture on the OP9-DLL1 monolayers) were harvested, centrifuged and transduced with the FOXP3GFP lentivirus at a multiplicity of infection (MOI) of 20 viral particles per cell in 500 µL of OP9 culture medium with cytokines for 40 minutes at 37° C. After transduction, the cells were seeded on new OP9-DLL1 monolayers in 2 mL of OP9 medium comprising the cytokines.

Flow Cytometry

The following conjugated antibodies were used for phenotyping and flow cytometry analysis: CD34-PeCY7, CD43-APC, KDR(CD309)-PE, CD7-PeCy5, CD5-BV510, CD3-APCCy7, TCRab-APC, CD4-BV605, CD8a-PE and CD8b-PeCy7 (ThermoFisher). All antibodies were used with a twentieth dilution. Dead cells were excluded from analysis in all experiments by labeling with DAPI. The fluorescence was measured with an LSR II or Canto II cytometer (BD Biosciences) and analyzed with the FLOWJO software (FlowJo LLC, Ashland, USA).

"DGE-RNA" RNA Sequencing

The RNeasy-Micro kit (Qiagen) was used to isolate total RNA which was then used to perform RNA sequencing. The 3'DGE protocol for RNA sequencing is the one described in Picarda et al. (2017).

Results

Figure 2:
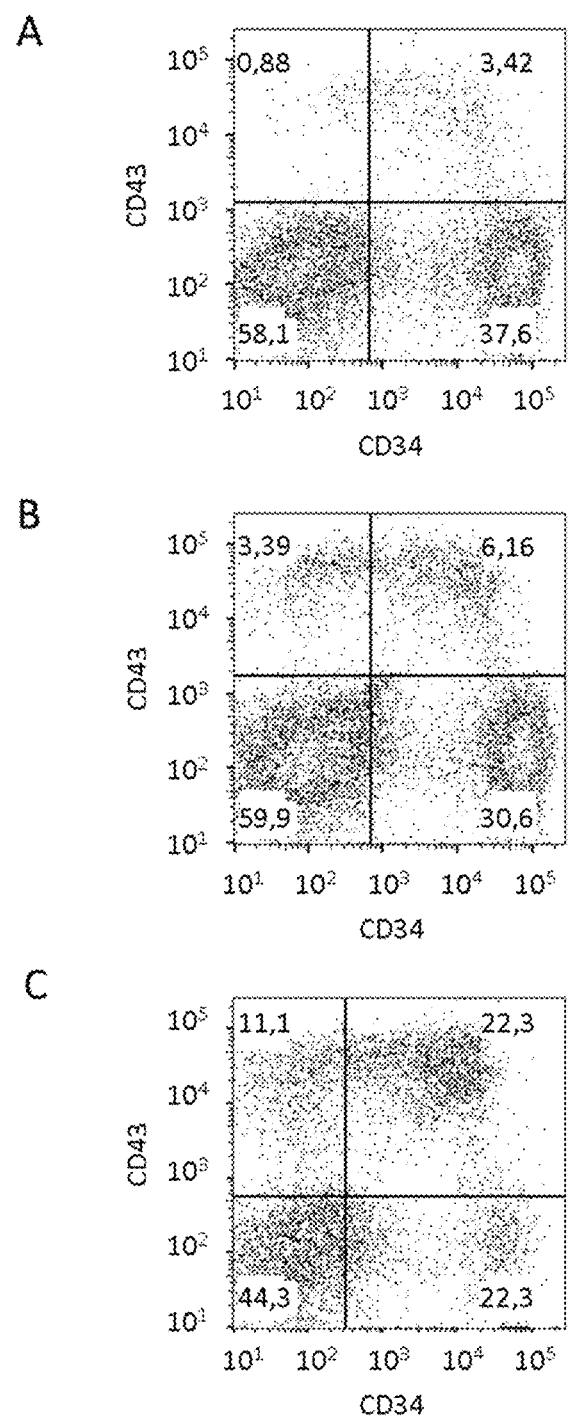
FIG. 2: cell phenotypes of embryoid bodies at D7, D8 and D9; Biparametric histograms for the presence of CD34 and CD43, markers of hematopoietic stem cells. A: measurement at D7. B: measurement at D8. C: measurement at D9.

FIG. 2 shows that after 7 days of culture of embryoid bodies (step 1 of the method of the invention), about 40% of the cells express CD34+. Between day 7 and day 9, the percentage of CD34+ cells in the population remains stable, and the percentage of CD43+ increases. On the $9^{th}$ day of development of embryoid bodies, the CD34+ cells express higher levels of transcription factors or key molecules for lymphoid differentiation such as Runx3, Ikaros, and IL-7R (results not shown).

Analysis by DGERNA-Seq sequencing showed that cells at D9 expressed Notch2. Expression of Notch1, Notch2NL, Notch3 and Notch4 was higher in CD34+CD43− cells than in CD34+CD43+ cells (results not shown), suggesting that these CD34+CD43− cells were more capable of differentiating, during the second phase, in coculture with the OP9-DLL1 cells thanks to the expression of the Notch molecules and the presence of the Notch DLL1 ligand in the culture medium.

The increase in the CD34+CD43+ subpopulation and the presence of the CD34+CD43− subpopulation in the embryoid bodies make the total cell population more able to differentiate during the second phase of cell culture.

Figure 3:
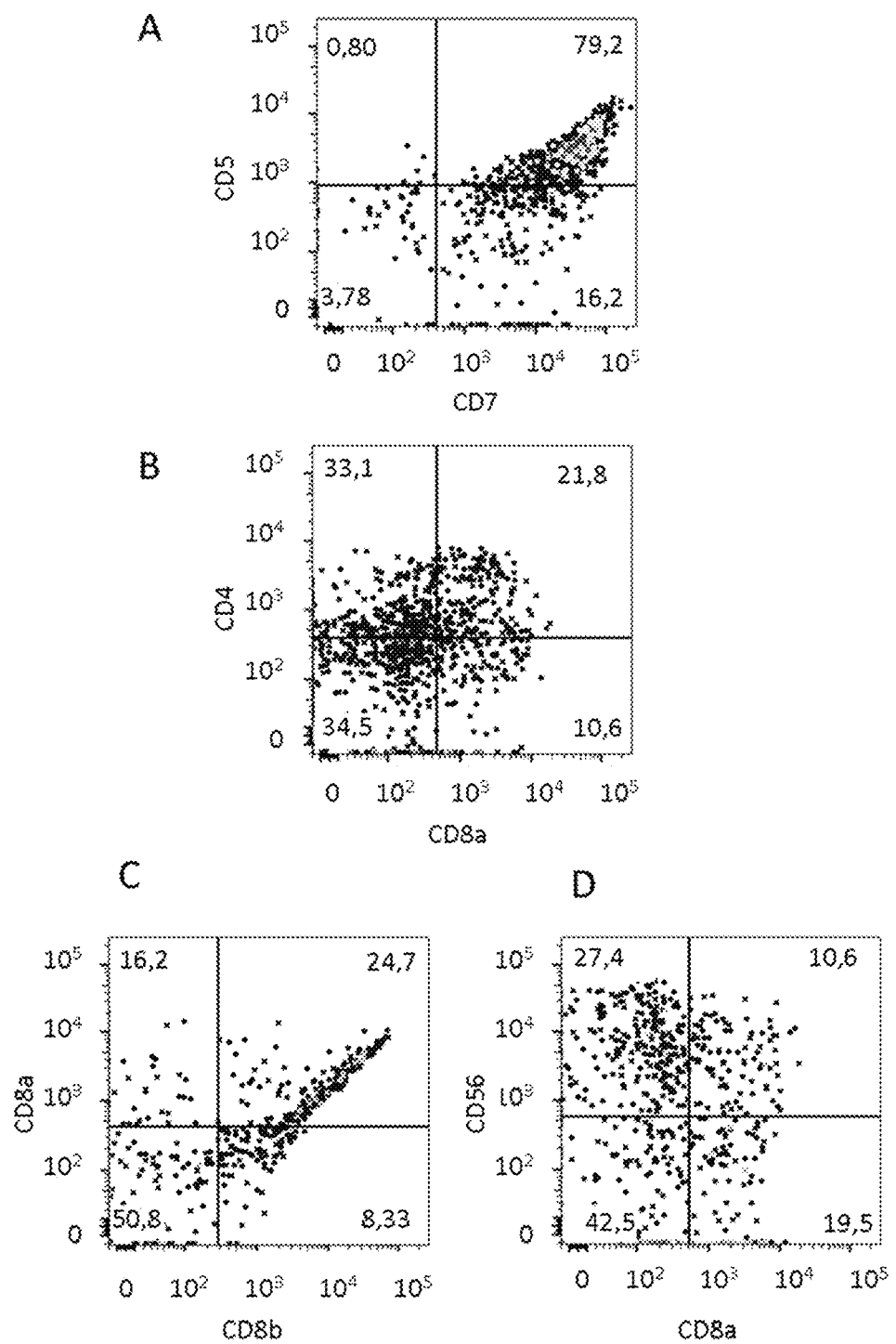
FIG. 3: cell phenotypes on day 20 of the differentiation phase (Dd20); Biparametric histograms for the presence at Dd20 of CD4, CD5, CD7, CD8a, CD8b and CD56 in the cell population for which the coculture was carried out at D9. A: expression of CD5 and CD7, markers of lymphoid cells. B: expression of CD4 and CD8a within the CD5+CD7+ subpopulation identified in A. C: expression of CD8a and CD8b within the CD5+CD7+ subpopulation identified in A. D: expression of CD56 and CD8a within the CD5+CD7+ subpopulation identified in A.

FIG. 3A shows expression of CD5 and CD7, markers of lymphoid lineage, by the cells at Dd20 (20th day of coculture with OP9 cells). About 80% of the cells are of the CD5+CD7+ phenotype; and among them, about 22% are CD4+CD8a+ (FIG. 3B), 25% are CD8a+CD8b+ (FIG. 3C), and 11% are CD56+CD8a+ (FIG. 3D).

Figure 4:
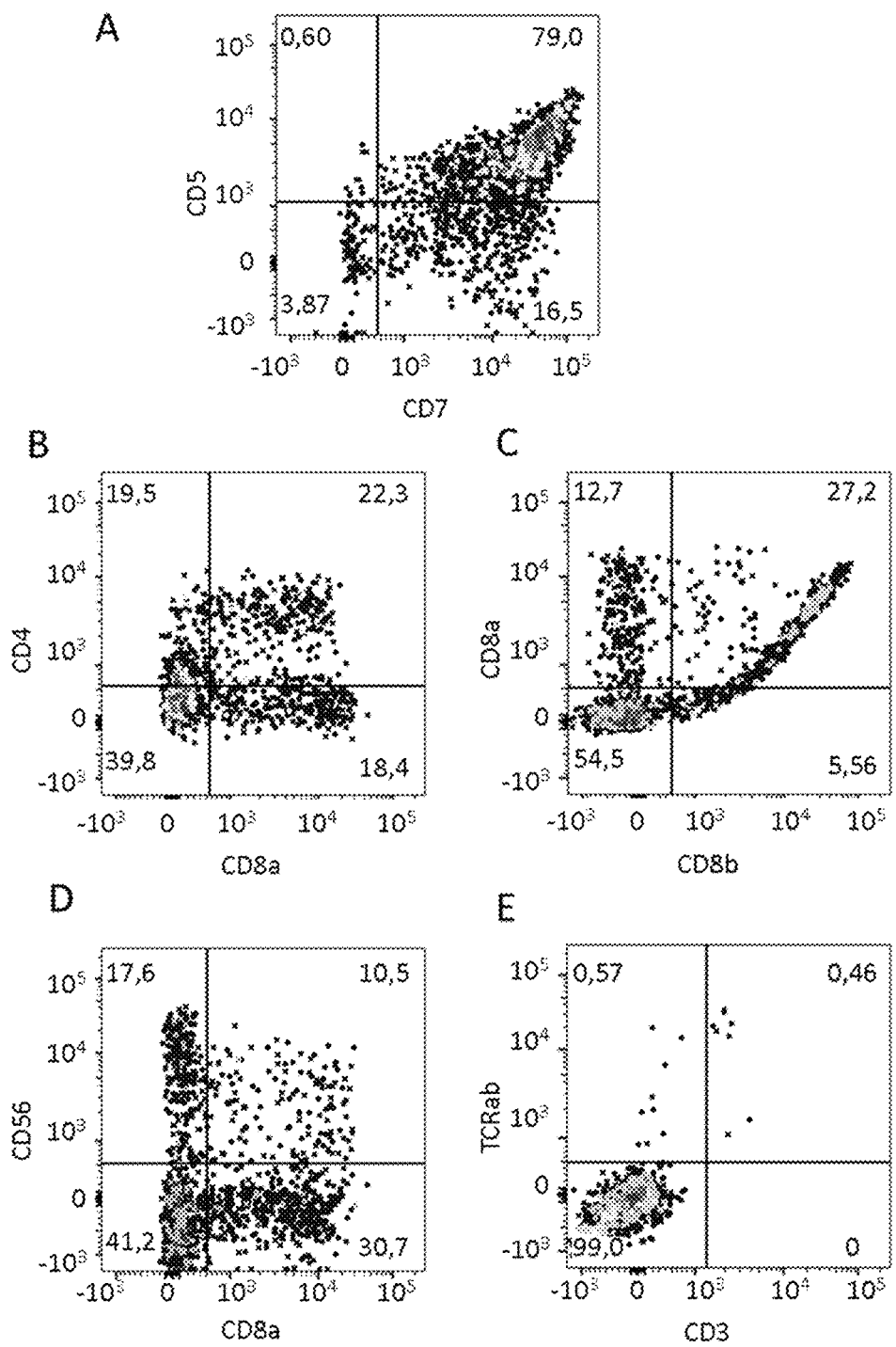
FIG. 4: cell phenotypes on day 26 of the differentiation phase (Dd26): biparametric histograms for the presence at Dd26 of CD3, CD4, CD5, CD7, CD8a, CD8b, CD56 and TCRab in the cell population for which the coculture was performed at D9. A: expression of CD5 and CD7, markers of lymphoid cells. B: expression of T cell markers CD4 and CD8a within the CD5+CD7+ subpopulation identified in A. C: expression of the T cell markers CD8a and CD8b within the CD5+CD7+ subpopulation identified in A. D: expression of NK and T cell markers CD56 and CD8a within the CD5+CD7+ subpopulation identified in A. E: expression of the T cell markers CD3 and TCRab within the CD5+CD7+ subpopulation identified in A.

FIG. 4A shows on the other hand the expression of CD5 and CD7 by the cells at Dd26 ($26^{th}$ day of coculture with OP9 cells). About 80% of the cells are of the CD5+CD7+ phenotype; and among them, about 22% are CD4+CD8a+ (FIG. 4B), 27% are CD8a+CD8b+ (FIG. 4C), and 11% are CD56+CD8a+ (FIG. 4D). Less than 1% of the population expresses TCRab and CD3 (FIG. 4E). In addition, DGE-RNA sequencing showed that the cells did not express Foxp3, the key transcription factor for Treg cells.

Figure 5:
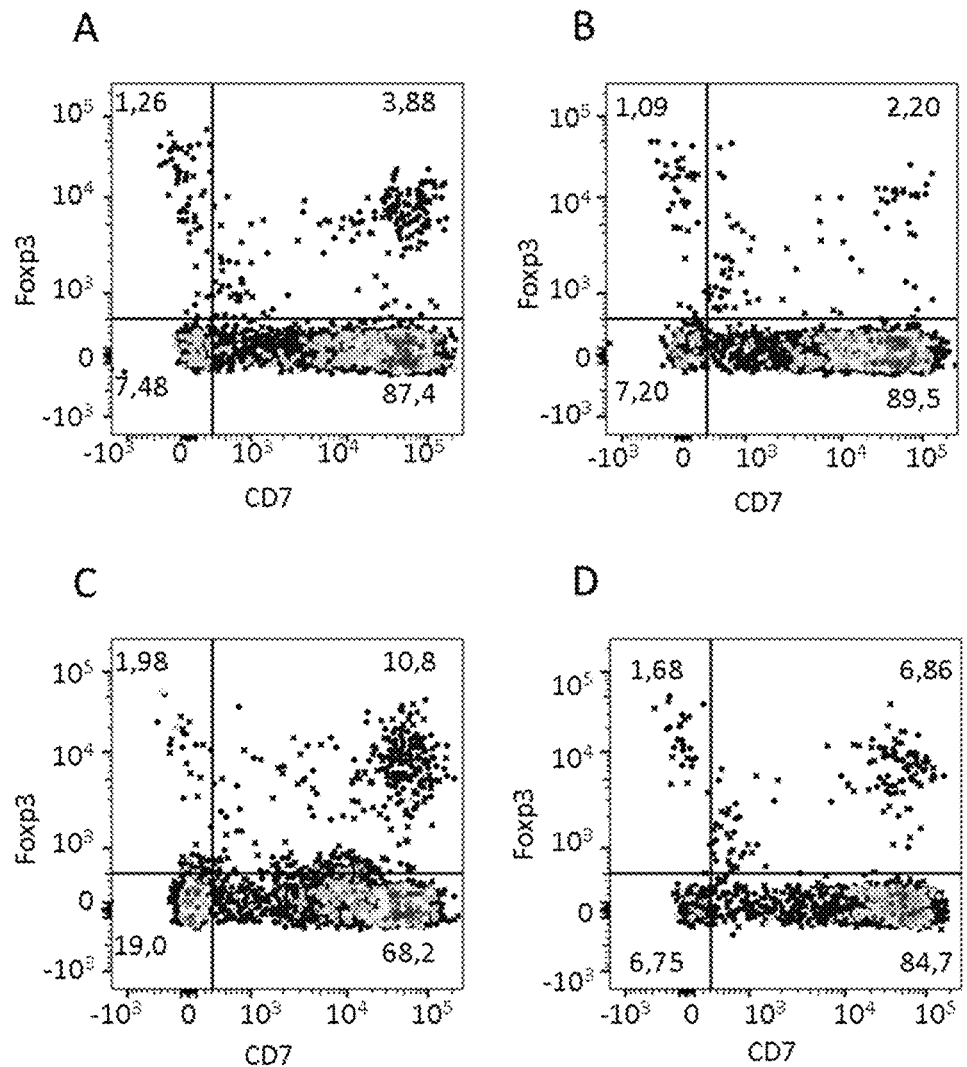
FIG. 5: cell phenotypes on day 26 of the differentiation phase (Dd26): biparametric histograms for the presence at Dd26 of Foxp3 and CD7 in the cell population for which the coculture was carried out at D9 and the transduction of Foxp3 took place at different times from the coculture start. A: results for transduction at Dd0. B: results for transduction at Dd5. C: results for transduction at Dd10. D: results for transduction at Dd15.

Thus, the introduction of the gene encoding Foxp3 was carried out to allow cells to differentiate into Treg cells. The insertion of the gene encoding Foxp3 was carried out by transduction of a lentivirus. Different times were chosen to perform the transduction of the cells, from the start of their coculture with OP9 cells: Dd0 (time of the start of coculture), Dd5 (5 days after the start of coculture), Dd10 (10 days after the start of coculture) and Dd15 (15 days after the start of coculture), then analyzed on Dd26. FIG. 5 shows that transduced cells were observed in each of these transductions. It appears that the transductions carried out at Dd10 (FIG. 5C) result in the obtaining of a greater number of cells expressing Foxp3, with approximately 11% of the CD7+Foxp3+ population.

Figure 6:
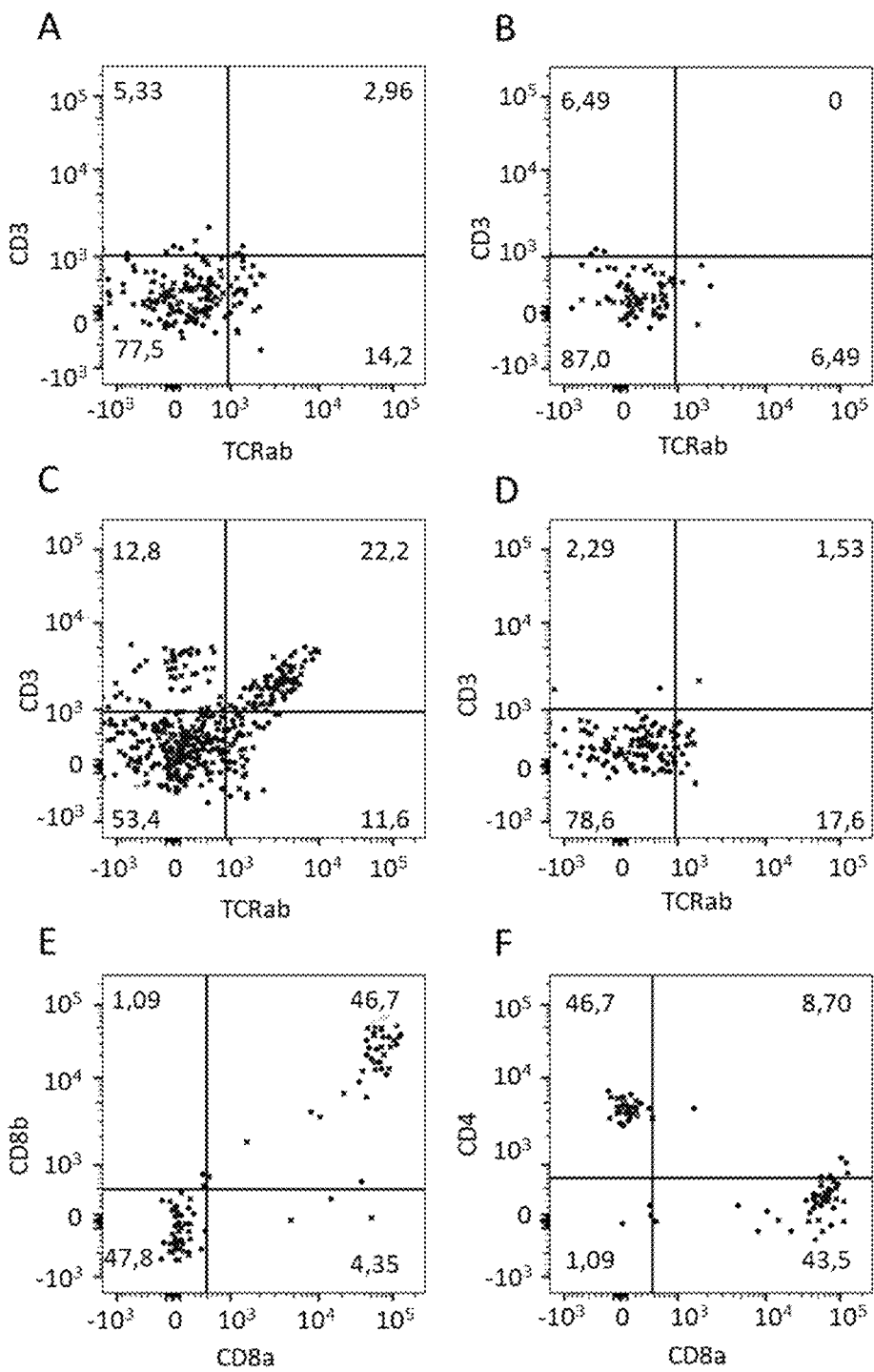
FIG. 6: cell phenotypes on day 26 of the differentiation phase (Dd26): biparametric histograms for the presence at Dd26 of CD3, CD4, CD8a, CD8b and TCRab in the cell subpopulations Foxp3+CD7+ identified in FIG. 5. A: expression of CD3 and TCRab when transduction took place at Dd0. B: expression of CD3 and TCRab when transduction took place at Dd5. C: expression of CD3 and TCRab when transduction took place at Dd10. D: expression of CD3 and TCRab when transduction took place at Dd15. E: expression of CD8a and CD8b in the CD3+TCRab+ subpopulation identified in C (transduction at Dd10). F: expression of CD8a and CD4 in the CD8a+CD8b+ subpopulation identified in E (transduction at Dd10).

The markers of this subpopulation of CD7+Foxp3+ cells are observed at Dd26 for each transduction time. Populations that were transduced at Dd10 comprise about 22% of CD7+Foxp3+ cells expressing CD3 and TCR (FIG. 6C), whereas populations that were transduced at Dd0, Dd5, Dd15 include less than 5% (respectively, FIGS. 6A, B and D). Half of the double positive cells transduced at Dd10 express CD8a (FIG. 6E) and the other half CD4 (FIG. 6F). Practically all cells expressing CD8a also express CD8b (FIG. 6E). Thus, the inventors have succeeded in obtaining Treg cells having the Foxp3+CD3+TCRab+CD8+ and Foxp3+CD3+TCRab+CD4+ phenotype.

Figure 7:
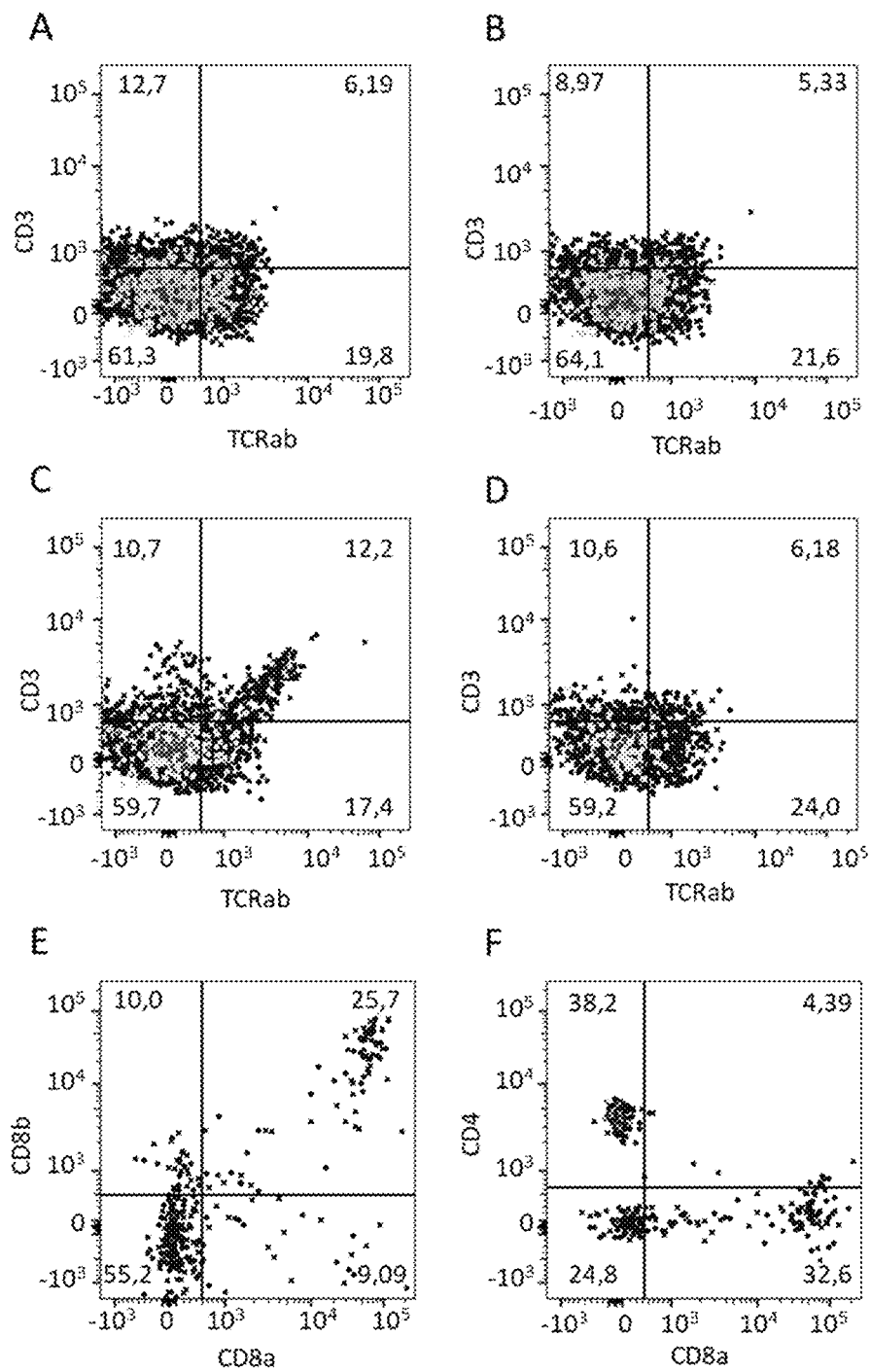
FIG. 7: cell phenotypes on day 26 of differentiation (Dd26): biparametric histograms for the presence at Dd26 of CD3, CD4, CD8a, CD8b and TCRab in the Foxp3−CD7+ cell subpopulations identified in FIG. 5. A: expression of CD3 and TCRab when transduction took place at Dd0. B: expression of CD3 and TCRab when transduction took place at Dd5. C: expression of CD3 and TCRab when transduction took place at Dd10. D: expression of CD3 and TCRab when transduction took place at Dd15. E: expression of CD8a and CD8b in the CD3+TCRab+ subpopulation identified in C (transduction at Dd10). F: expression of CD8a and CD4 in the CD8a+CD8b+ subpopulation identified in E (transduction at Dd10).

The markers of the CD7+Foxp3− cell subpopulation (FIG. 5) are observed at Dd26 for each transduction time. Populations that were transduced at Dd10 comprise about 12% CD7+Foxp3− cells expressing CD3 and TCR (FIG. 7C), while populations that were transduced at Dd0, Dd5, Dd15 comprise between about 5 and 7% (respectively, FIGS. 7 A, B and D). About 35% of these double positive cells express CD8a (FIG. 7E), 38% express CD4 (FIG. 7F), and about a quarter are double-negative CD4−CD8−. About 70% of the CD8a+ cells also express CD8b (FIG. 7E). These cells would be effector T cells.

Figure 8:
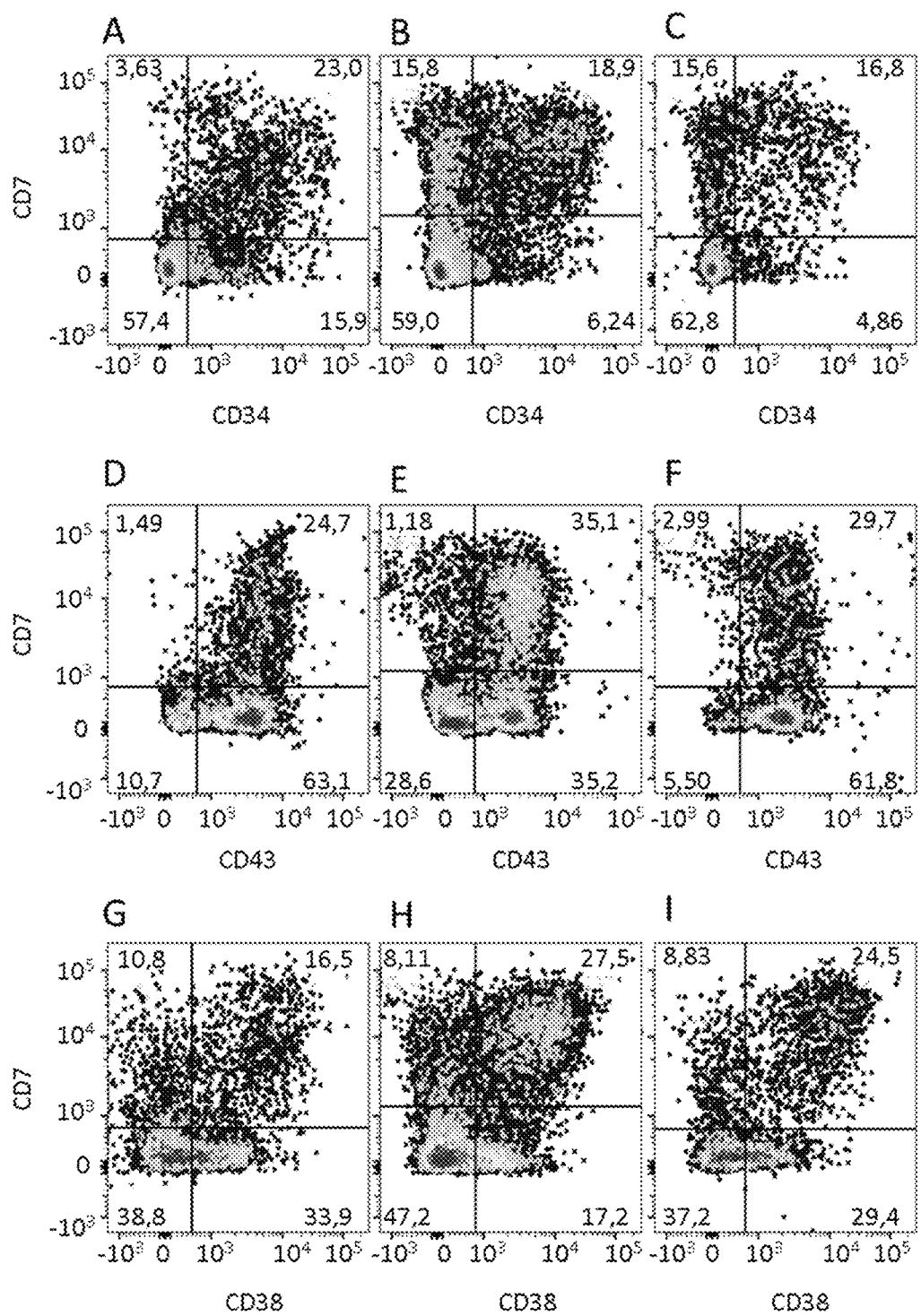
FIG. 8: cell phenotypes on day 26 of differentiation (Dd26): biparametric histograms for the presence of CD7, CD34, CD38, CD43 in the cell population for which the coculture was carried out at D9, in the absence of transduction. A: expression of CD7 and CD34 at Dd8. B: expression of CD7 and CD34 at Dd10. C: expression of CD7 and CD34 at Dd12. D: expression of CD7 and CD43 at Dd8. E: expression of CD7 and CD43 at Dd10. F: expression of CD7 and CD43 at Dd12. G: expression of CD7 and CD38 at Dd8. H: expression of CD7 and CD38 at Dd10. I: expression of CD7 and CD38 at Dd12.

To better understand the reason why cells are more receptive to transduction at Dd10, their phenotype was analyzed by flow cytometry. The results are shown in FIG. 8. Between Dd8 and Dd12, cells lose expression of CD34, a marker for hematopoietic stem cells, which reflects their passage to the lymphoid lineage. They acquire the CD7 marker, which stands for early lymphoid lineage, and they also express CD43 and CD38, which are markers for immune cells. At this stage, the cells do not yet express CD4 or CD8. It is possible to note that at Dd10, about 30% of the population becomes CD43− (FIG. 8E), while at Dd8 and Dd12, this percentage is only about 12 and 9% respectively (FIGS. 8D and F). Also, it is at Dd10 that the population comprises the greatest proportion of CD7+ and CD43+ cells (about 35%, FIG. 8E).

Example 2

The protocol for obtaining hematopoietic stem cells (Phase I) described in Example 1 from commercial hES WA09 stem cells (WiCell) was implemented from hES WA01 cells (WiCell), hiPS T04 (CRTUPFiPSC Nantes), hiPS LON80 (PFiPSC Nantes).

Figure 9:
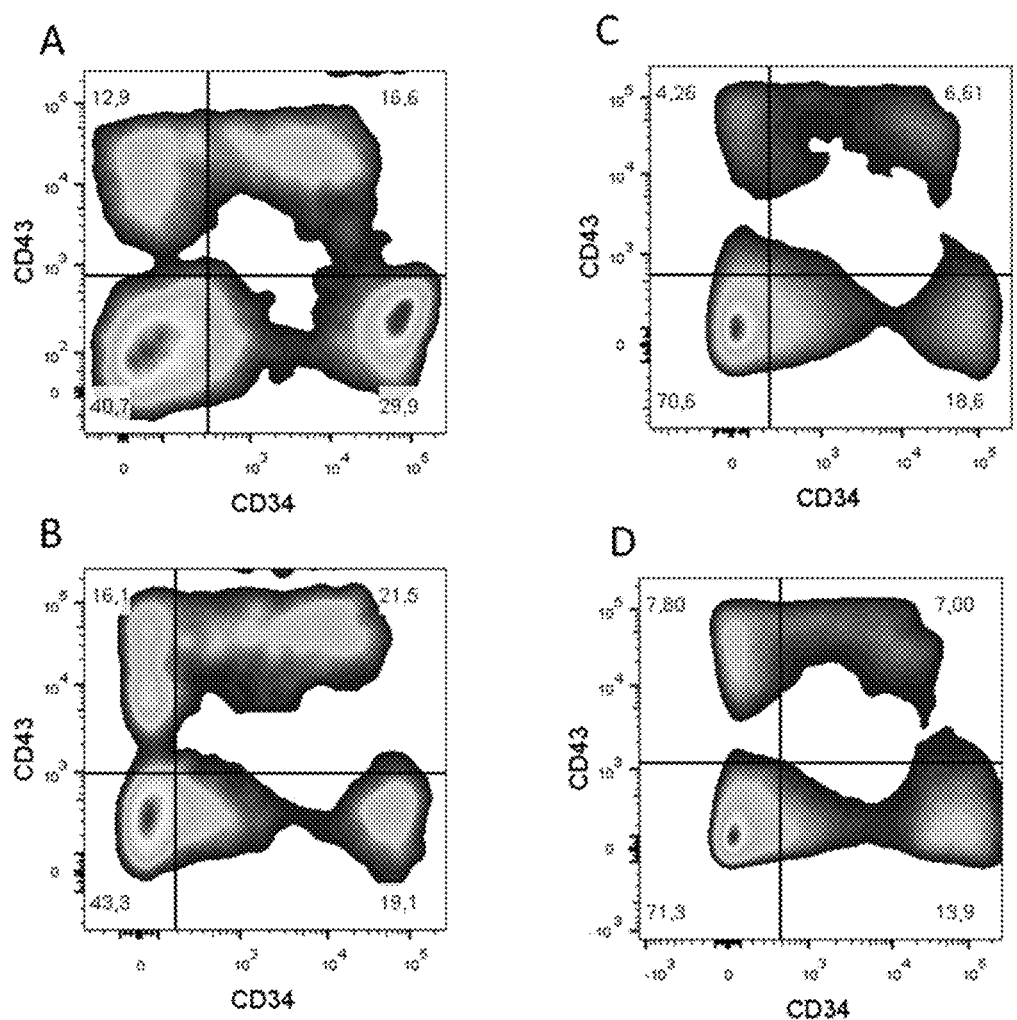
FIG. 9: cell phenotypes of the embryoid bodies at D9, obtained from distinct hES cell lines and hiPS cell lines: biparametric histograms for the presence of CD34 and CD43, hematopoietic stem cell markers. A: hES WA09. B: hiPS T04. C: hiPS LON80. D: hES WA01.

FIG. 9A confirms that hES WA09 cells can be differentiated into CD34+ hematopoietic stem cells (approximately 36% at D9), and shows that the proportion of CD34+CD43+ reaches about 16.5%. FIG. 9B shows that hiPS T04 cells can be differentiated into CD34+ hematopoietic stem cells (about 40% at D9), and that the proportion of CD34+CD43+ cells is about 21.5%. FIGS. 9C and 9D show that hiPS LON80 and hES WA01 cells can be differentiated into CD34+ hematopoietic stem cells and that the proportion of CD34+CD43+ cells reaches about 6.5% and 7.0%, respectively.

BIBLIOGRAPHY

Baine I, Basu S, Ames R, Sellers R, Macian F. (2013) Helios induces epigenetic silencing of 112 gene expression in regulatory T cells. J Immunol. 190(3): 1008-1016.

Bonini C, Mondino A. (2015) Adoptive T-cell therapy for cancer: The era of engineered T cells. Eur J Immunol. 45(9):2457-69.

Cavazzana-Calvo Marina, Six Emmanuelle, André-Schmutz Isabelle, Coulombel Laure. (2007) Hématopoïèse humaine: des cellules CD34 aux lymphocytes T. Med Sci: 23 (2): 151-160.

Chang C W, Lai Y S, Lamb L S Jr, Townes T M. (2014) Broad T-cell receptor repertoire in T-lymphocytes derived from human induced pluripotent stem cells. PLoS One. 9(5):e97335.

Chung Y, Klimanskaya I, Becker S, Li T, Maserati M, Lu S J, Zdravkovic T, Ilic D, Genbacev O, Fisher S, Krtolica A, Lanza R. (2008) Human embryonic stem cell lines generated without embryo destruction. Cell Stem Cell. 2(2):113-7.

Gill S, June C H. (2015) Going viral: chimeric antigen receptor T-cell therapy for hematological malignancies. Immunol Rev. 263(1):68-89.

Haque Rizwanul, Lei Fengyang, Xiong Xiaofang, et al. (2012) Programming of regulatory T cells from pluripotent stem cells and prevention of autoimmunity. *The Journal of Immunology,* 189(3): 1228-1236.

Haque, Mohammad et al. (2016) "Development of Stem Cell-Derived Antigen-Specific Regulatory T Cells Against Autoimmunity." Journal of visualized experiments: JoVE 117: 10.3791/54720.

Holmes R, Zúñifiga-Pflücker J C. (2009) The OP9-DL1 system: generation of T-lymphocytes from embryonic or hematopoietic stem cells in vitro. Cold Spring Harb Protoc. Feb; 2009(2): pdb.prot5156.

Jensen M C, Riddell S R. (2015) Designing chimeric antigen receptors to effectively and safely target tumors. Curr Opin Immunol. 33:9-15.

Kato Shingo, Jay A Berzofsky, Masaki Terabe. (2018) "Possible Therapeutic Application of Targeting Type II Natural Killer T Cell-Mediated Suppression of Tumor Immunity." Frontiers in Immunology 9: 314.

Lei F, Haque R, Weiler L, Vrana K E, Song J. (2009) T lineage differentiation from induced pluripotent stem cells. Cell Immunol. 260(1):1-5.

MacDonald K G, Hoeppli R E, Huang Q, Gillies J, Luciani D S, Orban P C, Broady R, Levings M K. (2016) Alloantigen-specific regulatory T cells generated with a chimeric antigen receptor. J Clin Invest. 126(4):1413-24

Passerini, Laura, Rosa Bacchetta. (2017) "Forkhead-Box-P3 Gene Transfer in Human CD4+ T Conventional Cells for the Generation of Stable and Efficient Regulatory T Cells, Suitable for Immune Modulatory Therapy." Frontiers in Immunology 8: 1282.

Picarda E, Bézie S, Boucault L, Autrusseau E, Kilens S, Meistermann D, Martinet B, Daguin V, Donnart A, Charpentier E, David L, Anegon I, Guillonneau C. (2017) Transient antibody targeting of CD45R C induces transplant tolerance and potent antigen-specific regulatory T cells. JCI Insight. 2(3):e90088.

Srivastava S, Riddell S R. (2015) Engineering CAR-T cells: Design concepts. Trends Immunol. 36(8):494-502.

The invention claimed is:

1. A method for obtaining a population of T cells from pluripotent stem cells, comprising the following steps:
   a) culturing pluripotent stem cells under conditions allowing to obtain embryoid bodies comprising at least 5% of CD34+CD43+cells;
   b) dissociating said embryoid bodies;
   c) culturing said dissociated embryoid bodies with at least one Notch ligand; and
   d) carrying out, during step c), the introduction between day Dd8 and day Dd12 of step c) of a vector comprising at least one nucleic acid sequence encoding Foxp3 in at least one cell.

2. The method according to claim 1, wherein step c) of culturing the dissociated embryoid bodies with at least one Notch ligand is carried out by coculturing the dissociated embryoid bodies with cells expressing at least one Notch ligand.

3. The method according to claim 1, wherein step d) of introducing a vector is carried out when at least 15% of the cell population exhibits the CD43− phenotype.

4. The method according to claim 1, wherein the embryoid bodies comprise at least 15% of CD34+CD43+ cells.

5. The method according to claim 1, wherein step a) is carried out for at least 9 days.

6. The method according to claim 1, wherein step a) is carried out for 9 to 12 days.

7. The method according to claim 1, wherein step a) is carried out in a serum free culture medium comprising BMP, FGF2, VEGF, SCF, Flt3-L and/or IL-3.

8. The method according to claim 1, wherein the dissociated embryoid bodies, obtained at the end of step b), are cultured in a culture medium comprising SCF, Flt3-L and/or IL-7, for at least 15 days.

9. The method according to claim 1, wherein the vector of step d) is a retrovirus.

10. The method according to claim 1, wherein the vector of step d) is a lentivirus.

11. The method according to claim 1, wherein the nucleic acid sequence of the vector of step d) comprises a further nucleic acid sequence of interest.

12. The method according to claim 11, wherein the further nucleic acid of interest is selected from a nucleic acid encoding a chimeric antigen receptor (CAR), Mcl-1, Bcl-xL, and Helios.

13. The method according to claim 1, wherein the pluripotent stem cells are human induced pluripotent stem cells or human embryonic stem cells.

14. The method according to claim 1, comprising an additional step of isolating a cell population selected from regulatory T cells (Treg), effector T lymphocytes (Teff), and CD4−CD8−CD3+TCRab+T lymphocytes.

* * * * *